US007569573B2

(12) United States Patent
Nair et al.

(10) Patent No.: US 7,569,573 B2
(45) Date of Patent: Aug. 4, 2009

(54) DIKETO ACIDS WITH NUCLEOBASE SCAFFOLDS: ANTI-HIV REPLICATION INHIBITORS TARGETED AT HIV INTEGRASE

(75) Inventors: Vasu Nair, Athens, GA (US); Guochen Chi, Athens, GA (US); Vinod R. Uchil, Athens, GA (US)

(73) Assignee: The University of Georgia Research Foundation, Inc., Athens, GA (US)

( * ) Notice: Subject to any disclaimer, the term of this patent is extended or adjusted under 35 U.S.C. 154(b) by 31 days.

(21) Appl. No.: 11/820,444

(22) Filed: Jun. 19, 2007

(65) Prior Publication Data
US 2007/0259823 A1 Nov. 8, 2007

Related U.S. Application Data

(62) Division of application No. 11/047,229, filed on Jan. 31, 2005, now Pat. No. 7,250,421.

(51) Int. Cl.
*C07D 473/28* (2006.01)
*C07D 473/36* (2006.01)
*C07D 473/40* (2006.01)
*C07D 473/00* (2006.01)
*A61K 31/52* (2006.01)
*A61P 31/18* (2006.01)
*C07D 403/04* (2006.01)
*C07D 405/04* (2006.01)
*C07D 413/04* (2006.01)
*C07D 417/04* (2006.01)
*C07D 419/04* (2006.01)

(52) U.S. Cl. .................. 514/263.1; 514/263.2; 544/264
(58) Field of Classification Search .................. 544/264; 514/263.1, 263.2
See application file for complete search history.

(56) References Cited

U.S. PATENT DOCUMENTS

| 6,492,423 B1 | 12/2002 | Sergio et al. |
| 6,620,841 B1 | 9/2003 | Fujishita et al. |
| 6,645,956 B1 | 11/2003 | Fujishita et al. |
| 6,803,374 B2 | 10/2004 | Priestley et al. |
| 6,803,378 B2 | 10/2004 | Walker et al. |
| 7,098,201 B2 | 8/2006 | Fujishita et al. |
| 2003/0207922 A1 | 11/2003 | Neuner et al. |
| 2005/0026902 A1 | 2/2005 | Maziasz |

FOREIGN PATENT DOCUMENTS

WO    WO 00/06529    2/2000

OTHER PUBLICATIONS

Vasu Nair Rev, Med. Viro. 12;179-193, 2002.*
Fauci, Science 239, 617-622 (1988).
Katz & Skalka, Annu. Rev. Biochem. 63, 133-173 (1994).
Frankel, Annu. Rev. Biochem. 67, 1-25 (1998).
De Clercq, J. Med. Chem 38, 2491-2517 (1995).
De Clercq, Clin. Microbiol Rev. 10, 674-693 (1997).
De Clercq, Nature Reviews: Drug Discovery 11, 13-25 (2002).
Johnson & Gerber, in "Advances in Internal Medicine" vol. 44, Mosby: St. Louis, 1-40 (2000).
Miller & Hazuda, Current Opinion in Microbiology, 4, 535-539 (2001).
Asante-Appiah & Skalka, Adv. Virus Res., 52, 351-369 (1999).
Nair, in "Recent Advances in Nucleosides: Chemistry and Chemotherapy," Elsevier Science: Netherlands, 149-166 (2002).
DeClercq, Intl. J. Biochem, Cell Biol. 36, 1800-1822 (2004).
Nair, Rev. Med. Virol., 12, 179-193 (2002).
Nair, Current Pharmaceutical Design, 9, 2553-2565 (2003).
Esposito & Craigie, Adv. Virus Res. 52,319-333 (1999).
Chi and Nair, Bioorg. Med. Chem. Letter 14, 4815-4817 (2004).
Taktakishvilli et al., J. Am. Chem. Soc., 122, 5671-5677 (2000).
Wai et al., "4- Aryl-2,4-dioxobutanoic acid inhibitors of HIV-1 integrase and viral replication in cells," J. Med. Chem. 43, 4923-4926 (2000).
Pais, G. C. G., et al., "Structure activity of 3-aryl-1,3-diketo-containing compounds as HIV-1 integrase inhibitors" J. Med. Chem. 45, 3184-3194 (2002).
Marchand, C. jet al., "Structural determinants for HIV-1 integrase inhibition by beta-diketo acids" J. Biol. Chem. 277, 12596-12603 (2002).
Sechi, M. etal., "Design and Synthesis of novel indole beta-diketo acid derivatives as HIV-1 integrase inhibitors." J. Med. Chem. 47, 5298-5310 (2004).
Zhang, et al., "Azido-containing aryl beta-keto acid HIV-1 integrase inhibitors" Bioorg. Med. Chem. Lett. 13, 1214-1219 (2003).
Grobler, J. A. et al., Proc. Natl. Acad. Sci. U.S.A. 99, 6661-6666 (2002).
Hazuda, D. J. et al., Science 287, 646-650 (2000).
Pannecouque, C. et al., Current Biology 12, 1169-1177 (2002).
Nair et al., "HIV Integrase Inhibitors with Nucleobase Scaffolds: Discovery of a Highly Potent Anti-HIV Agent", J. Med. Chem; 2006; 49:445-447.

* cited by examiner

*Primary Examiner*—Venkataraman Balasubramanian
(74) *Attorney, Agent, or Firm*—Henry D. Coleman; R. Neil Sudol; William J. Sapone

(57) ABSTRACT

A new class of diketo acids constructed on nucleobase scaffolds, designed as inhibitors of HIV replication through inhibition of HIV integrase, is described. These compounds are useful in the prevention or treatment of infection by HIV and in the treatment of AIDS and ARC, either as the compounds, or as pharmaceutically acceptable salts, with pharmaceutically acceptable carriers, used alone or in combination with antivirals, immunomodulators, antibiotics, vaccines, and other therapeutic agents. Methods of treating AIDS and ARC and methods of treating or preventing infection by HIV are also described.

31 Claims, No Drawings

DIKETO ACIDS WITH NUCLEOBASE SCAFFOLDS: ANTI-HIV REPLICATION INHIBITORS TARGETED AT HIV INTEGRASE

This application is a divisional application of Ser. No. 11/047,229, filed Jan. 31, 2005, now U.S. Pat. No. 7,250,421.

BACKGROUND OF THE INVENTION

The human immunodeficiency virus, HIV, encodes three key viral enzymes through its pol gene and these enzymes are critical for the replication of this virus [Fauci, *Science*, 239, 617-622 (1988); Katz & Skalka, *Annu. Rev. Biochem.*, 63, 133-173 (1994); Frankel, *Annu. Rev. Biochem.*, 67, 1-25 (1998)]. For this reason, these enzymes of the pol gene have been targeted as potential sites of attack in the development of HIV antiviral chemotherapeutic agents [De Clercq, *J. Med. Chem.* 38, 2491-2517 (1995); *Clin. Microbiol. Rev.*, 10, 674-693 (1997); De Clercq, *Nature Reviews: Drug Discovery*, 11, 13-25 (2002)]. Drug discovery involving two of these enzymes, HIV reverse transcriptase (RT) and HIV protease (PR), and subsequent clinical applications of some of these therapeutic agents in combination therapy for the treatment of acquired immunodeficiency syndrome (AIDS) and AIDS related complex (ARC) in HAART (highly-active antiretroviral therapy) have suggested that this methodology of targeting key viral enzymes represents a useful approach in antiviral chemotherapy [Johnson & Gerber, in "Advances in Internal Medicine," vol. 44. Mosby: St. Louis, 1-40 (2000); De Clercq, *Nature Reviews: Drug Discovery*, 11, 13-25 (2002); Miller & Hazuda, *Current Opinion in Microbiology*, 4, 535-539 (2001); Asante-Appiah & Skalka, *Adv. virus Res.*, 52, 351-369 (1999); Nair, in "Recent Advances in Nucleosides: Chemistry and Chemotherapy," Elsevier Science: Netherlands, 149-166 (2002); DeClercq, *Intl. J. Biochem. Cell Biol.* 36, 1800-1822 (2004)]. While HIV RT and HIV PR have been extensively studied with respect to therapeutics, the third enzyme of the pol gene, HIV integrase, has received much less consideration [Miller & Hazuda, *Current Opinion in Microbiology*, 4, 535-539 (2001); Nair, *Rev. Med Virol.*, 12, 179-193 (2002); Nair, *Current Pharmaceutical Design*, 9, 2553-2565 (2003)].

At present there are no drugs in clinical use for HIV/AIDS where the mechanism of action is inhibition of HIV integrase. HIV-1 integrase is a protein of 32 kDa encoded at the 3'-end of the pol gene [Asante-Appiah & Skalka. *Adv. Virus Res.*, 52, 351-369 (1999); Esposito & Craigie, *Adv. Virus Res.*, 52, 319-333 (1999)]. It is involved in the integration of HIV DNA into the host cell chromosome. Because integrase has no human counterpart and because it plays the significant role of completing the invasion of the human cell by HIV, it is an attractive target for the discover), of inhibitors of therapeutic potential.

Incorporation of HIV DNA into host chromosomal DNA in the cell nucleus catalyzed by integrase apparently occurs by a specifically defined sequence of 3'-processing or tailoring and strand transfer/integration reactions [Asante-Appiah & Skalka, *Adv. Virus Res.*, 52, 351-369 (1999); Esposito & Craigie *Adv. Virus Res.*, 52, 319-333 (1999)]. Prior to the initiation of the integration process, there is assembly of viral DNA, previously produced by reverse transcription, on the integrase. HIV integrase recognizes specific sequences in the LTRs of viral DNA. Following assembly of viral DNA on integrase, the processing of viral DNA occurs where there is site specific endonuclease activity and two nucleotides are cleaved off from each 3'-end of the double helical viral DNA to produce the tailored viral DNA recessed by two nucleotides and bearing a terminal CAOH-3'. For this initial 3'-processing step, integrase apparently activates the phosphodiester bond towards cleavage. The recessed viral DNA thus produced is joined in the next step to host cell DNA in the nucleus through a trans-esterification reaction. In this step, integrase positions the 3'-OH end of the viral DNA for nucleophilic attack on the phosphodiester bond in the host DNA. In the subsequent step, there is cleavage of 4-6 bp in host DNA and the coupling involves the joining of processed CAOOH-3' viral DNA ends to the 5'-phosphate ends of the host DNA. Finally, there is repair of the resulting gapped intermediate mediated by host cell enzymes, although a role here for the integrase is also possible.

A variety of compounds are inhibitors of HIV integrase but some of these compounds are non-specific inhibitors of the enzyme while evidence suggests that others may possess some specificity. The various classes include nucleotides, oligonucleotides, dinucleotides, and miscellaneous small molecules including heterocyclic systems, natural products, diketo acids, sulfones and others [Nair, *Rev. Med. Virol.*, 12, 179-193 (2002); Nair, *Current Pharmaceutical Design*, 9, 2553-2565 (2003); Chi and Nair, Bioorg. Med. Chem. Lett. 14, 4815-4817 (2004); Nair and coworkers, *J. Am. Chem. Soc.*, 122, 5671-5677 (2000)].

The class of previously studied compounds that are most directly relevant to this patent are diketo acids with aryl or heteroaryl substitutions. Some of these compounds are inhibitors of HIV integrase, but most commonly of only the strand transfer step. The integrase inhibition data have been reported in several scientific publications [Wai, et al., "4-Aryl-2,4-dioxobutanoic acid inhibitors of HIV-1 integrase and viral replication in cells," *J. Med. Chem.* 43, 4923-4926 (2000); Pais, G. C. C., et al., "Structure activity of 3-aryl-1, 3-diketo-containing compounds as HIV-1 integrase inhibitors." *J. Med. Chem.* 45, 3184-3194 (2002); Marchand, C., et al., "Structural determinants for HIV-1 integrase inhibition by β-diketo acids," *J. Biol. Chem.* 277, 12596-12603 (2002); Sechi, M., et al., "Design and synthesis of novel indole beta-diketo acid derivatives as HIV-1 integrase inhibitors," *J. Med. Chem.* 47, 5298-5310 (2004); Zhang, et al., "Azido-containing aryl β-keto acid HIV-1 integrase inhibitors," *Bioorg. Med. Chem. Lett.* 13, 1215-1219 (2003)]. Other publications in the area are of peripheral relationship to this patent application.

The mechanism of inhibition of HIV integrase by diketo acids may be the result of interaction of the functional groups on these compounds with metal ions in the active site of integrase, resulting in a functional sequestration of these critical metal cofactors [Grobler, J. A., et al., *Proc. Natl. Acad. Sci. U.S.A.* 99, 6661-6666 (2002)].

The most directly related patents to this application are: Selnick, H. G. et al., (Merck & Co. Ltd.), "Preparation of nitrogen-containing 4-heteroaryl-2,4-dioxobutyric acids useful as HIV integrase inhibitors," WO 9962513; Young, S. D., et al., (Merck & Co. Ltd.), "Preparation of aromatic and heteroaromatic 4-aryl-2,4-dioxobutyric acid derivatives useful as HIV integrase inhibitors," WO 9962897; Fujishita, T., et al., Yoshinaga, T., et al. (Shionogi & Co. Ltd.), "Preparation of aromatic heterocycle compounds having HIV integrase inhibiting activities," WO 0039086; Akihiko, S., (Shionogi & Co. Ltd.), "Medicinal compositions containing propenone derivatives," WO 0196329; Payne, L. S., et al., (Merck & Co. Ltd.; Tularik, Inc.), "Preparation of 1,3-diaryl-1,3-propanediones as HIV integrase inhibitors," WO 0100578; Egbertson, M., et al., (Merck & Co. Ltd.), "HIV integrase inhibitors," WO 9962520.

Some of the patents cited above are closely related. However, none of the patents or publications describe the class of compounds according to the present invention. In particular, compounds according to the present invention have a nucleic acid base (nucleobase) scaffold, which is a requirement for potent activity and which was not previously recognized.

Structures of the three most active compounds described in previous patents and publications are shown below. They are representative of the best of the previously known inhibitors. They inhibit the strand transfer step in the HIV integrase assay but do not show significant inhibition of the 3'-processing step of integrase action.

In vitro anti-HIV activity data

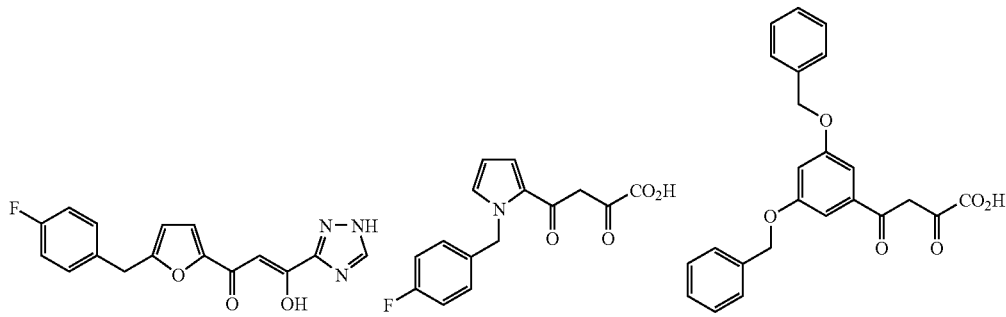

| Compd. No: | S-1360 | L-731988 | L-708906 |
|---|---|---|---|
| $IC_{50}$ (μM): | 0.14* | 1.0 | 5.5** |
| $CC_{50}$ (μM): | 110* | Not Given | 88.3** |
| Therapeutic Index | 786* | Not Given | 16** |
| Patents: | WO 0196329 | WO 9962513 | WO 9962520 |
| Publications: |  | Hazuda, D. J., et al., Science 287, 646-650 (2000) | Hazuda, D. J., et al., Science 287, 646-650 (2000) |

*Anti-HIV-1 data of Yoshinaga et al from Proc. 9$^{th}$ Conference on Retroviruses and Opportunistic Infections, 2002 (no 8, p 55) cited by DeClercq, Int. J. Biochem. & Cell Biol., 36, 1800-1822 (2004).

**These in vitro anti-HIV-1 data were reported for compound L-708906 by the DeClercq laboratory [Pannecouque, C., et al., Current Biology, 12, 1169-1177 (2002)].

However, the class of compounds described by us in this invention is not only significant because of the strong inhibition of both the 3'-processing and strand transfer steps of HIV integrase, but also because of its enhanced potency and therapeutic index as evidenced by in vitro anti-HIV activity. Critical in the design of our compounds is the nucleic acid base (nucleobase) scaffold, which is a requirement for potent activity and which was not previously recognized.

As an example, in a side by side in vitro anti-HIV activity comparison with AZT (PBMC cell-based assay), the compound of the present invention shown below with a uracil scaffold (see also general formula I) had a therapeutic index of >10,000 and was more active than AZT (therapeutic index=5,511). This compound is also far more active than the anti-HIV integrase inhibitors previously described in the publications and patents cited above. The therapeutic index of the best known HIV integrase inhibitor previously reported (see compound number S-1360 in Table above) in vitro anti-HIV assays was only 786.

In Vitro Anti-HIV Activity Data for a Compound of this Invention

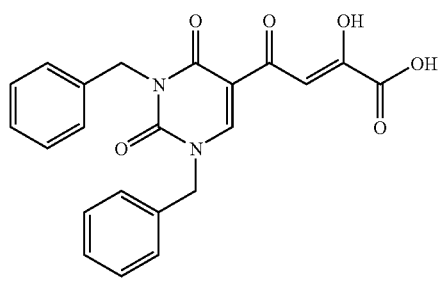

$IC_{50}$ 0.02 μM
$CC_{50}$ >200 μM
Therapeutic Index >10,000

SUMMARY OF THE INVENTION

A new class of diketo acids constructed on nucleobase scaffolds, and designed as inhibitors of HIV replication through inhibition of HIV integrase, is described. These compounds can be represented by the general formula I (and includes tautomers, regioisomers, geometric isomers and optical isomers thereof, as well as pharmaceutically acceptable salts thereof, where applicable), in which the moiety illustrated as a square is a molecular scaffold made up of a nucleic acid base (nucleobase) derivative. These compounds have application in the prevention or treatment of infection by HIV and the treatment of AIDS and ARC, either as the compounds, or as their pharmaceutically acceptable salts, with pharmaceutically acceptable carriers, used alone or in combination with antivirals, immunomodulators, antibiotics, vaccines, and other therapeutic agents. Methods of treating AIDS and ARC and methods of treating or preventing infection by HIV are also described.

DETAILED DESCRIPTION OF THE INVENTION

The following terms shall be used throughout the specification to describe the present invention. Unless otherwise indicated, a term used to describe the present invention shall be given its ordinary meaning as understood by those skilled in the art.

The term "compound", as used herein, unless otherwise indicated, refers to any specific chemical compound disclosed herein and includes tautomers, regioisomers, geometric isomers, and where applicable, optical isomers thereof, as well as pharmaceutically acceptable salts thereof,. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds.

The term "patient" or "subject" is used throughout the specification to describe an animal, generally a mammal and preferably a human, to whom treatment, including prophylactic treatment, with the compositions according to the present invention is provided. For treatment of those infections, conditions or disease states which are specific for a specific animal such as a human patient, the term patient refers to that specific animal.

The term "effective" is used herein, unless otherwise indicated, to describe an amount of a compound or composition which, in context, is used to produce or effect an intended result, whether that result relates to the treatment of a viral, microbial or other disease state, disorder or condition associated with HIV, ARC or AIDS or alternatively, is used to produce another compound, agent or composition. This term subsumes all other effective amount or effective concentration terms which are otherwise described in the present application.

The term "nucleobase scaffold" is used throughout the specification to mean a nucleoside base selected from uracil, xanthine, hypoxanthine and purine which contain at least four substituents at four substitutable positions on the nucleoside base, one of which is a ketoacid as otherwise defined herein and the other three of which $R^1$, $R^2$ and $R^3$, are as defined herein.

The term "heteroaryl" shall mean a 5 or 6-membered heteroaromatic ring containing 1 to 2 heteroatoms selected from oxygen, nitrogen and sulfur, which heteroaromatic ring is optionally substituted with from 1 to 3 substituents such as halogen, hydroxyl, $C_{1-3}$ alkyl, $C_{1-3}$ alkoxy and $CF_3$. The terms heteroaryl and "heteroaromatic ring" are used interchangeably herein.

The term "human immunodeficiency virus" or "HIV" shall be used to describe human immunodeficiency viruses 1 and 2 (HIV-1 and HIV-2).

The terms "ARC" and "AIDS" refer to syndromes of the immune system caused by the human immunodeficiency virus, which are characterized by susceptibility to certain diseases and T cell counts which are depressed compared to normal counts. HIV progresses from Category 1 (Asymptomatic HIV Disease) to Category 2 (ARC), to Category 3 (AIDS), with the severity of the disease.

A Category 1 HIV infection is characterized by the patient or subject being HIV positive, asymptomatic (no symptoms) and having never had fewer than 500 CD4 cells. If the patient has had any of the AIDS-defining diseases listed for categories 2 (ARC) or 3 (AIDS), then the patient is not in this category. If the patient's t-cell count has ever dropped below 500, that patient is considered either Category 2 (ARC) or Category 3 (AIDS).

A Category 2 (ARC) infection is characterized by the following criteria: The patient's T-cells have dropped below 500 but never below 200, and that patient has never had any Category 3 diseases (as set forth below) but have had at least one of the following defining illnesses—
Bacillary angiomatosis
Candidiasis, oropharyngeal (thrush)

Candidiasis, vulvovaginal; persistent, frequent, or poorly responsive to therapy Cervical dysplasia (moderate or severe)/cervical carcinoma in situ Constitutional symptoms, such as fever (38.5 C) or diarrhea lasting longer than 1 month Hairy leukoplakia, oral Herpes zoster (shingles), involving at least two distinct episodes or more than one dermatome Idiopathic thrombocytopenic purpura Listeriosis Pelvic inflammatory disease, particularly if complicated by tubo-ovarian abscess Peripheral neuropathy According to the U.S. government, in Category 2 ARC, the immune system shows some signs of damage but it isn't life-threatening.

A Category 3 (AIDS) infection is characterized by the following criteria:

your T-cells have dropped below 200 or you have had at least one of the following defining illnesses—

Candidiasis of bronchi, trachea, or lungs

Candidiasis, esophageal

Cervical cancer, invasive**

Coccidioidomycosis, disseminated or extrapulmonary

Cryptococcosis, extrapulmonary

Cryptosporidiosis, chronic intestinal (greater than 1 month's duration)

Cytomegalovirus disease (other than liver, spleen, or nodes)

Cytomegalovirus retinitis (with loss of vision)

Encephalopathy, HIV-related

Herpes simplex: chronic ulcer(s) (greater than 1 month's duration); or bronchitis, pneumonitis, or esophagitis Histoplasmosis, disseminated or extrapulmonary Isosporiasis, chronic intestinal (greater than 1 month's duration)

Kaposi's sarcoma

Lymphoma, Burkitt's (or equivalent term)

Lymphoma, immunoblastic (or equivalent term)

Lymphoma, primary, of brain

*Mycobacterium* avium complex or *M. kansasii*, disseminated or extrapulmonary

*Mycobacterium tuberculosis*, any site (pulmonary** or extrapulmonary)

*Mycobacterium*, other species or unidentified species, disseminated or extrapulmonary

*Pneumocystis carinii* pneumonia

Pneumonia, recurrent**

Progressive multifocal leukoencephalopathy

*Salmonella septicemia*, recurrent

Toxoplasmosis of brain

Wasting syndrome due to HIV

The term "coadministration" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, provided that effective concentrations of all coadministered compounds or compositions are found in the subject at a given time.

The present invention is directed to compounds of the general molecular formula I, combinations thereof, or pharmaceutically acceptable salts thereof, in the inhibition of HIV integrase, the prevention or treatment of HIV infections and in the treatment of AIDS and ARC. Compounds of formula I are defined as follows:

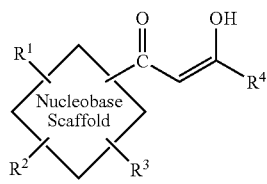

including tautomers, regioisomers, geometric isomers, and where applicable, optical isomers thereof and pharmaceutically acceptable salts thereof, wherein the nucleobase scaffold and R groups are defined as:

(i) keto acids with uracil nucleobase scaffold;

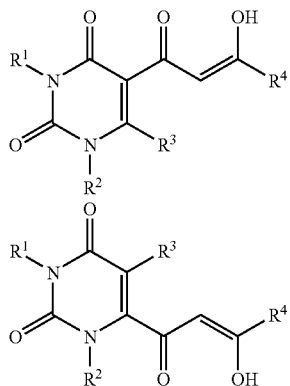

$R^1$ and $R^2$ are independently:
a) H,
b) $C_{1-6}$ alkyl,
c) $C_{1-6}$ fluoroalkyl,
d) $C_{1-6}$ alkyl $S(O)_n R$, wherein n selected from 0-2, R is selected from $C_{1-3}$ alkyl, phenyl and substituted phenyl with substituents selected from:
  1) halogen,
  2) hydroxy,
  3) $C_{1-3}$ alkyl,
  4) $C_{1-3}$ alkoxy,
  5) $CF_3$,
e) $C_{5-6}$ cycloalkyl with 1 to 3 substituents selected from:
  1) halogen,
  2) hydroxy,
  3) $C_{1-3}$ alkyl,
  4) $C_{1-3}$ alkoxy,
  5) $CF_3$,
f) $C_{1-6}$ alkenyl,
g) $C_{1-6}$ alkyl $CO_n R^a$, wherein n selected from 1 and 2, $R^a$ selected from:
  1) $C_{1-6}$ alkyl,
  2) H,
h) Phenyl,
i) Substituted phenyl with 1 to 3 substituents selected from:
  1) halogen,
  2) hydroxy,
  3) $C_{1-3}$ alkyl, 4) $C_{1-3}$ alkoxy,
5) $CF_3$,
j) Benzyl,
k) Substituted benzyl with 1 to 3 substituents selected from:
  1) halogen,
  2) hydroxy,
  3) $C_{1-3}$ alkyl,
  4) $C_{1-3}$ alkoxy,
  5) $CF_3$,
l) $C_{2-6}$ alkyl substituted with phenyl,
m) $C_{2-6}$ alkyl substituted with phenyl, the phenyl group may be substituted with 1 to 3 substituents selected from:
  1) halogen,
  2) hydroxy,
  3) $C_{1-3}$ alkyl,
  4) $C_{1-3}$ alkoxy,
  5) $CF_3$,
n) $R^b$,
o) $C_{1-6}$ alkyl substituted with $R^b$,
Wherein each $R^b$ is 5 or 6 membered heteroaromatic ring containing 1 to 2 heteroatoms selected from oxygen, nitrogen and sulfur, the ring could be substituted or not on carbon or nitrogen with 1 to 3 substituents selected from:
  1) halogen,
  2) hydroxy,
  3) $C_{1-3}$ alkyl,
  4) $C_{1-3}$ alkoxy,
  5) $CF_3$,
$R^3$ is selected from:
  a) H,
  b) $C_{1-6}$ alkyl,
  c) Halogen,
  d) Hydroxyl,
  e) Phenylthio,
  f) Substituted phenylthio with 1 to 3 substituents selected from:
    1) halogen,
    2) hydroxy,
    3) $C_{1-3}$ alkyd,
    4) $C_{1-3}$ alkoxy,
    5) $CF_3$,
  g) Benzyl,
  h) Substituted benzyl with 1-3 substituents selected from:
    1) halogen,
    2) hydroxy,
    3) $C_{1-3}$ alkyl,
    4) $C_{1-3}$ alkoxy,
    5) $CF_3$,
$R^4$ is selected from:
  a) $CO_2R^c$, wherein $R^c$ is selected from:
    1) $C_{1-6}$ alkyl,
    2) H,
    3) sodium or other pharmaceutical acceptable salt,
  b) $P(O)(OR^d)(OR^e)$, wherein $R^d$ and $R^e$ could be same or not that are selected from:
    1) $C_{1-6}$ alkyl,
    2) H,
    3) sodium or other pharmaceutical acceptable salt.

(ii) keto acids with xanthine nucleobase scaffold;

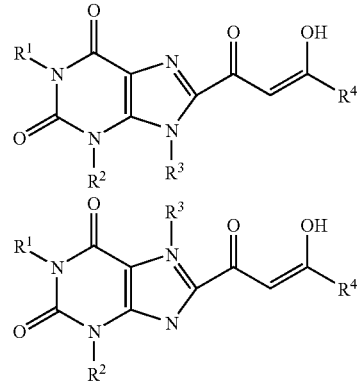

$R^1$, $R^2$ and $R^3$ are independently:
  a) H,
  b) $C_{1-6}$ alkyl,
  c) $C_{1-6}$ fluoroalkyl,
  d) $C_{1-6}$ alkyl $S(O)_nR$, wherein n selected from 0-2, R selected from $C_{1-3}$ alkyl, phenyl and substituted phenyl with substituents selected from:
    1) halogen,
    2) hydroxy,
    3) $C_{1-3}$ alkyl,
    4) $C_{1-3}$ alkoxy,
    5) $CF_3$,
  e) $C_{5-6}$ cycloalkyl with 1 to 3 substituents selected from:
    1) halogen,
    2) hydroxy,
    3) $C_{1-3}$ alkyl,
    4) $C_{1-3}$ alkoxy,
    5) $CF_3$,
  f) $C_{1-6}$ alkenyl,
  g) $C_{1-6}$ alkyl $CO_nR^a$, wherein n selected from 1 and 2, $R^a$ selected from:
    1) $C_{1-6}$ alkyl,
    2) H,
  h) Phenyl,
  i) Substituted phenyl with 1 to 3 substituents selected from:
    1) halogen,
    2) hydroxy,
    3) $C_{1-3}$ alkyl,
    4) $C_{1-3}$ alkoxy,
    5) $CF_3$,
  j) Benzyl,
  k) Substituted benzyl with 1 to 3 substituents selected from:
    1) halogen,
    2) hydroxy,
    3) $C_{1-3}$ alkyl,
    4) $C_{1-3}$ alkoxy.
    5) $CF_3$,
  l) $C_{2-6}$ alkyl substituted with phenyl,
  m) $C_{2-6}$ alkyl substituted with phenyl, the phenyl group may be substituted with 1 to 3 substituents selected from:
    1) halogen,
    2) hydroxy,
    3) $C_{1-3}$ alkyl,
    4) $C_{1-3}$ alkoxy,
    5) $CF_3$, n) $R^b$,
o) $C_{1-6}$ alkyl substituted with $R^b$, Wherein each $R^b$ is 5 or 6 membered heteroaromatic ring containing 1 to 2 heteroatoms selected from oxygen, nitrogen and sulfur, the ring could be substituted or not on carbon or nitrogen with 1 to 3 substituents selected from:
1) halogen,
2) hydroxy,
3) $C_{1-3}$ alkyl,
4) $C_{1-3}$ alkoxy,
5) $CF_3$, $R^4$ is selected from:
a) $CO_2R^c$, wherein $R^c$ is selected from:
1) $C_{1-6}$ alkyl,
2) H,
3) sodium or other pharmaceutical acceptable salt,
b) $P(O)(OR^d)(OR^e)$, wherein $R^d$ and $R^e$ could be same or not that are selected from:
1) $C_{1-6}$ alkyl,
2) H,
3) sodium or other pharmaceutical acceptable salt.

(iii) keto acids with hypoxanthine nucleobase scaffold;

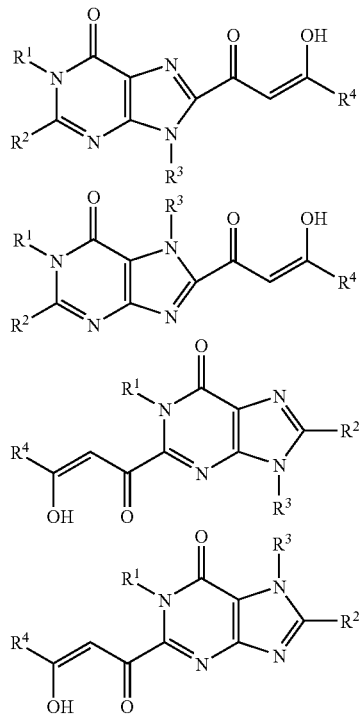

$R^1$, $R^2$ and $R^3$ are independently:
a) H,
b) $C_{1-6}$ alkyl,
c) $C_{1-6}$ fluoroalkyl,
d) $C_{1-6}$ alkyl $S(O)_nR$, wherein n selected from 0-2, R selected from $C_{1-3}$ alkyl, phenyl and substituted phenyl with substituents selected from:
1) halogen,
2) hydroxy,
3) $C_{1-3}$ alkyl,
4) $C_{1-3}$ alkoxy,
5) $CF_3$,
e) $C_{5-6}$ cycloalkyl with 1 to 3 substituents selected from:
1) halogen,
2) hydroxy,
3) $C_{1-3}$ alkyl,
4) $C_{1-3}$ alkoxy,
5) $CF_3$,
f) $C_{1-6}$ alkenyl,
g) $C_{1-6}$ alkyl $CO_nR^a$, wherein n selected from 1 and 2, $R^a$ selected from:
1) $C_{1-6}$ alkyl,
2) H,
h) Phenyl,
i) Substituted phenyl with 1 to 3 substituents selected from:
1) halogen,
2) hydroxy,
3) $C_{1-3}$ alkyl,
4) $C_{1-3}$ alkoxy,
5) $CF_3$,
j) Benzyl,
k) Substituted benzyl with 1 to 3 substituents selected from:
1) halogen,
2) hydroxy,
3) $C_{1-3}$ alkyl,
4) $C_{1-3}$ alkoxy,
5) $CF_3$,
l) $C_{2-6}$ alkyl substituted with phenyl,
m) $C_{2-6}$ alkyl substituted with phenyl, the phenyl group may be substituted with 1 to 3 substituents selected from:
1) halogen,
2) hydroxy,
3) $C_{1-3}$ alkyl,
4) $C_{1-3}$ alkoxy,
5) $CF_3$,
n) $R^b$,
o) $C_{1-6}$ alkyl substituted with $R^b$, Wherein each $R^b$ is 5 or 6 membered heteroaromatic ring containing 1 to 2 heteroatoms selected from oxygen, nitrogen and sulfur, the ring could be substituted or not on carbon or nitrogen with 1 to 3 substituents selected from:
1) halogen,
2) hydroxy,
3) $C_{1-3}$ alkyl,
4) $C_{1-3}$ alkoxy,
5) $CF_3$, $R^4$ is selected from:
a) $CO_2R^c$, wherein $R^c$ is selected from:
1) $C_{1-6}$ alkyl,
2) H,
3) sodium or other pharmaceutical acceptable salt,
b) $P(O)(OR^d)(OR^e)$, wherein $R^d$ and $R^e$ could be same or not that are selected from:
1) $C_{1-6}$ alkyl,
2) H,
3) sodium or other pharmaceutical acceptable salt.

(iv) keto acids with purine nucleobase scaffold;

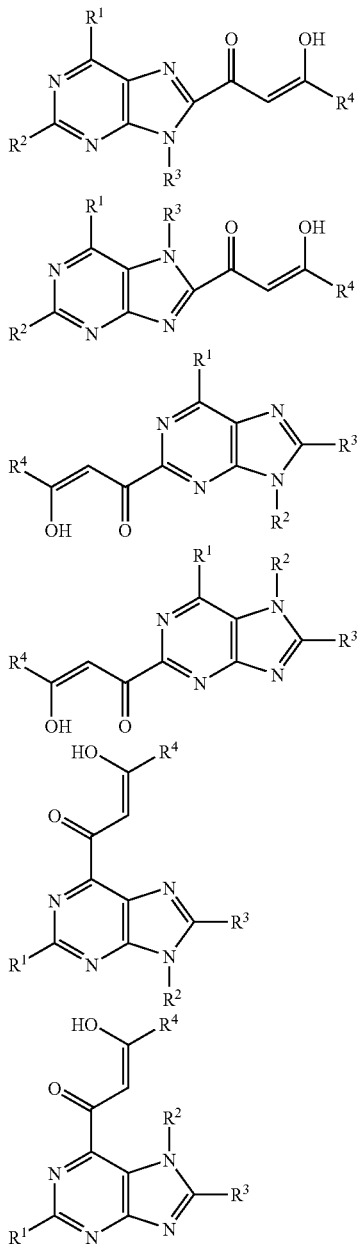

$R^1$, $R^2$ and $R^3$ are independently:
a) H,
b) $C_{1-6}$ alkyl,
c) $C_{1-6}$ fluoroalkyl,
d) $C_{1-6}$ alkyl $S(O)_nR$, wherein n selected from 0-2, R selected from $C_{1-3}$ alkyl, phenyl and substituted phenyl with substituents selected from:
  1) halogen,
  2) hydroxy,
  3) $C_{1-3}$ alkyl,
  4) $C_{1-3}$ alkoxy,
  5) $CF_3$,
e) $C_{5-6}$ cycloalkyl with 1 to 3 substituents selected from:
  1) halogen,
  2) hydroxy,
  3) $C_{1-3}$ alkyl,
  4) $C_{1-3}$ alkoxy,
  5) $CF_3$,
f) $C_{1-3}$ alkenyl,
g) $C_{1-6}$ alkyl $CO_nR^a$, wherein n selected from 1 and 2, $R^a$ selected from:
  1) $C_{1-6}$ alkyl,
  2) H,
h) Phenyl,
i) Substituted phenyl with 1 to 3 substituents selected from:
  1) halogen,
  2) hydroxy,
  3) $C_{1-3}$ alkyl,
  4) $C_{1-3}$ alkoxy,
  5) $CF_3$,
j) Benzyl,
k) Substituted benzyl with 1 to 3 substituents selected from:
  1) halogen,
  2) hydroxy,
  3) $C_{1-3}$ alkyl,
  4) $C_{1-3}$ alkoxy,
  5) $CF_3$,
l) $C_{2-6}$ alkyl substituted with phenyl,
m) $C_{2-6}$ alkyl substituted with phenyl, the phenyl group may be substituted with 1 to 3 substituents selected from:
  1) halogen,
  2) hydroxy,
  3) $C_{1-3}$ alkyl,
  4) $C_{1-3}$ alkoxy,
  5) $CF_3$,
n) $R^b$,
o) $C_{1-6}$ alkyl substituted with $R^b$,
Wherein each $R^b$ is 5 or 6 membered heteroaromatic ring containing 1 to 2 heteroatoms selected from oxygen, nitrogen and sulfur, the ring could be substituted or not on carbon or nitrogen with 1 to 3 substituents selected from:
  1) halogen,
  2) hydroxy,
  3) $C_{1-3}$ alkyl,
  4) $C_{1-3}$ alkoxy,
  5) $CF_3$,
$R^4$ is selected from:
a) $CO_2R^c$, wherein $R^c$ is selected from:
  1) $C_{1-6}$ alkyl,
  2) H,
  3) sodium or other pharmaceutical acceptable salt,
b) $P(O)(OR^d)(OR^e)$, wherein $R^d$ and $R^e$ could be same or not that are selected from:
  1) $C_{1-6}$ alkyl,
  2) H,
  3) sodium or other pharmaceutical acceptable salt.

Also included within the present invention are pharmaceutical compositions useful for inhibiting HIV integrase, comprising of an effective amount of a compound of this invention, and a pharmaceutically acceptable carrier. Pharmaceutical compositions useful for treating infection by HIV or for treating AIDS or ARC are also included by the present invention. The present invention also includes methods for inhibiting the viral enzyme, HIV integrase, and a method of inhibiting HIV growth or replication, or treating an HIV infection or for treating AIDS or ARC. In addition, the present invention is directed to a pharmaceutical composition comprising, in combination, a therapeutically effective amount of a compound of the present invention in combination with a therapeutically effective amount of an agent for the treatment of AIDS selected from (i) an AIDS or HIV antiviral agent, (ii) an anti-infective agent, (iii) an immunomodulator, (iv) other useful therapeutic agents including antibiotics and other antiviral agents.

The compounds of the present invention may have regioisomers with respect to $R^1$, $R^2$ and $R^3$ and these regioisomeric forms are included in the present invention. The compounds of the present invention may have asymmetric centers and may occur as optical isomers and all of these isomeric forms are included in the present patent invention. The compounds may have geometric isomers and these forms are included in the present invention.

Tautomeric forms may also exist with compounds of the present invention. Thus, the terminology "and tautomers thereof" is used in describing tautomeric forms of compounds of formula I such as Ia and Ib (shown below). By naming compounds as

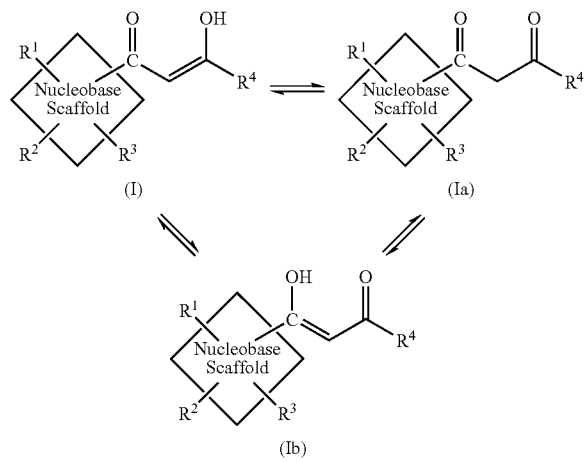

being represented by the general formula I and tautomers thereof, it is understood that for the purposes of the present invention that tautomers Ia and Ib are also included. Similarly, by referring to compound (Ia), it is understood for the purposes of the present application that the tautomers (I) and (Ib) are also intended. The same holds true for references to tautomer (Ib).

When the variables involving $R^1$, $R^2$, $R^3$, $R^4$ occur more than once in any formula I, its definition on each occurrence is independent of its definition at every other occurrence. Combinations of nucleobase and variables are permissible only if such combinations result in stable compounds.

The compounds of the present invention are useful in the inhibition of HIV integrase, the prevention or treatment of infection by HIV and in the treatment of the disease known as AIDS. Treating AIDS or preventing or treating infection by HIV is defined as including the treatment of a vide range of states of HIV infection: AIDS, ARC and actual or potential exposure to HIV (e.g., through blood transfusion, exchange of body fluids, bites, needle punctures, exposure to infected patient blood during medical or dental procedures, and other means).

Other applications are also part of this invention. For example, the compounds of this invention are useful in the preparation and execution of screening assays for antiviral compounds including in the isolation of viral enzyme mutants and in further understanding of the enzyme, HIV integrase.

The present invention also provides for the use of a compound of structural formula (I) to make a pharmaceutical composition useful for inhibiting HIV integrase and in the treatment of AIDS or ARC.

The compounds of the present invention may be administered in the form of "well-known pharmaceutically acceptable" salts. The latter is intended to include all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, camsylate, mucate, carbonate, napsylate, chloride, nitrate, clavulanate, N-methylglucamine, citrate, ammonium salt, dihydrochloride, oleate, edetate, oxalate, edisylate, pamoate, estolate, palmitate, esylate, fumarate, phosphate, diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and others which can be used as a dosage form for modifying the solubility or hydrolysis characteristics or can be used in sustained release or pro-drug formulations. The pharmaceutically acceptable salts of this invention include those with counterions such as sodium, potassium, calcium, lithium, magnesium, zinc, and from bases such as ammonia, ethylenediamine, N-methylglutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide.

Also, in the case of a carboxylic acid (—COOH) or an alcohol group being present, pharmaceutically acceptable esters can be employed, e.g., acetate, maleate, pivaloyloxymethyl and others, more preferably $C_1$-$C_{20}$ esters and those esters known in the art for improving solubility or hydrolysis characteristics for use as sustained release or pro-drug formulations. Pharmaceutically acceptable esters can also be employed in the case where a phosphonic acid group [—PO(OH)$_2$] is present. Diketo phosphonic acids attached to nucleobase scaffolds are also part of this invention.

Therapeutically effective amounts of the compounds of the present invention may be administered to patients orally, parenterally, by inhalation spray, or rectally, in dosage unit formulations containing pharmaceutically-acceptable carriers, adjuvants and vehicles including nanoparticle drug delivery approaches. The term "pharmaceutically acceptable" is meant to infer that the carrier, diluent or excipient must be compatible with the other ingredients of the formulation and not deleterious to the patient or recipient. Pharmaceutical compositions may be in the form of orally-administrable suspensions or tablets, nasal sprays and injectable preparations (injectable aqueous or oleagenous suspensions or suppositories). This method of treatment is part of the invention. The administration approaches used (orally as solution or suspension, immediate release tablets, nasal aerosol or inhalation, injectable solutions or suspensions or rectally administered in the form of suppositories) involve techniques that are well-known in the art of pharmaceutical formulation.

The compounds of this invention can be administered orally to humans in a preferred form (such as tablets) and in a preferred dosage range of about 0.1 to 200 mg/kg body weight in divided doses. The specific dose level and frequency of dosage for any particular patient may be varied and will depend upon a variety of factors including compound activity, compound metabolism and duration of action, patient age, body weight, general health, sex, diet, mode and time of administration, rate of excretion, drug combination, the severity of the particular condition, and the condition of the patient undergoing therapy.

The present invention also includes therapeutically effective combinations of the HIV integrase inhibitor compounds of formula I with one or more other therapeutic agents such as AIDS antivirals, other antiviral agents, immunomodulators, antiinfectives, antibiotics, vaccines or other therapeutic agents. Some examples are given below.

ANTIVIRAL AGENTS

| Drug Name | Manufacturer | Therapeutic Use |
|---|---|---|
| 097 | Hoechst/Bayer | HIV infection, AIDS, ARC (NNRT inhibitor) |
| Amprenivir 141W94, GW141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil AL-721 | Gilead Sciences Ethigen (Los Angeles, CA) | HIV infection ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which neutralizes pH labile alpha aberrant Interferon | Advanced Biotherapy Concepts (Rockville, MD) | AIDS, ARC |
| AR 177 | Aronex Pharm | HIV infection, AIDS, ARC |
| Beta-fluoro-ddA | National Cancer Institute | AIDS-associated diseases |
| BMS-232623 (CGP-73547) | Bristol-Myers Squibb/Novartis | HIV infection, AIDS, ARC (protease inhibitor) |
| BMS-234475 (CGP-61755) | Bristol-Myers Squibb/Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV Peripheral CMV Retinitis |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP-266) | DuPont Merck | HIV infection, AIDS, ARC (non-nucleoside RT inhibitor |
| EL10 | Elan Corp, PLC (Gainesville, GA) | HIV infection |
| Famciclovir | Smith Kline | Herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive; combination with AZT/ddI/ddC |
| ISIS-2922 | ISIS Pharmaceuticals | CMV retinitis |
| KNI-272 | Natl. Cancer Institute | HIV-associated diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CVV retinitis, HIV infection, other CMV |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydro-deoxythymidine | Bristol-Myers Squibb | HIV infection, AIDS, ARC |
| Valaciclovir | Glaxo Wellcome | Genital HSV & CMV infections |
| Virazole Ribavirin | Viratek/ICN (Costa Mesa, CA) | Asymptomatic HIV positive, LAS, ARC |
| VX-478 | Vertex | HIV infection, AIDS, ARC |
| Zalcitabine | Hoffmann-LaRoche | HIV infection, AIDS, ARC with AZT |

-continued

ANTIVIRAL AGENTS

| Drug Name | Manufacturer | Therapeutic Use |
| --- | --- | --- |
| Zidovudine; AZT | Glaxo Wellcome | HIV infection, AIDS, ARC, Kaposi's sarcoma, in combination with other therapies |
| Tenofovir diisoproxil fumarate salt (Viread ®) | Gilead | HIV infection, AIDS, (RT inhibitor) |
| Combivir ® | GSK | HIV infection, AIDS, (RT inhibitor) |
| Abacavir succinate (or Ziagen ®) | GSK | HIV infection, AIDS, (reverse transcriptase inhibitor) |
| Fuzeon ® (or T-20) | Roche/Trimeris | HIV infection, AIDS, viral Fusion inhibitor |

IMMUNO-MODULATORS

| Drug Name | Manufacturer | Therapeutic Use |
| --- | --- | --- |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246, 738 | American Cyanamid Lederle Labs | AIDS, Kaposi's sarcoma |
| EL10 | Elan Corp, PLC (Gainesville, GA) | HIV infection |
| FP-21399 | Fuki Immuno PHARM | Blocks HIV fusion with CD4+ cells |
| Gamma Interferon | Genentech | ARC, in combination w/TNF |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |

-continued

IMMUNO-MODULATORS

| Drug Name | Manufacturer | Therapeutic Use |
| --- | --- | --- |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4-IgG | Genentech | AIDS, ARC |
| rCD4-IgG Hybrids | | AIDS, ARC |
| Recombinant Soluble Human CD4 | Biogen | AIDS, ARC |
| Interferon Alfa 2a | Hoffman-LaRoche | Kaposi's sarcoma, AIDS, AR, combination w/AZT |
| SK&F1-6528 Soluble T4 | Smith Kline | HIV infection |
| Thymopentin | Immunobiology Research Institute (Annandale, NJ) | HIV infection |
| Tumor Necrosis Factor (TNF) | Genentech | ARC, in combination w/gamma Interferon |

ANTI-INFECTIVES

| Drug Name | Manufacturer | Therapeutic Use |
| --- | --- | --- |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine isethionate | Fisons Corporation | PCP prophylaxis |
| Spiramycin | Rhone-Poulenc | Cryptosporidial diarrhea |
| Intraconazole-R51211 | Janssen Pharm | Histoplasmosis; cryptococcal meningitis |
| Trimetrexate | Warner-Lambert | PCP |

OTHER AGENTS

| Drug Name | Manufacturer | Therapeutic Use |
| --- | --- | --- |
| Daunorubicin | NeXstar, Sequus | Karposi's sarcoma |
| Recombinant Human Erythropoietin | Ortho Pharm. Corp. | Severe anemia assocated w/AZT therapy |
| Recombinant Human Growth Hormone | Serono | AIDS-related wasting, cachexia |

-continued

OTHER AGENTS

| Drug Name | Manufacturer | Therapeutic Use |
|---|---|---|
| Megestrol Acetate | Bristol-Myers Squibb | Treatment of anorexia associated w/AIDS |
| Testosterone | Alza, Smith Kline | AIDS-related wasting |
| Total Enteral Nutrition | Norwich Eaton Pharmaceuticals | Diarrhea and malabsorption related to AIDS |

The combinations of the compounds of this invention with AIDS antivirals, other antivirals, immunomodulators, anti-infectives, antibiotics, vaccines, other therapeutic agents are not limited to the list in the above Table, but includes, in principle, any combination with any pharmaceutical composition useful for the treatment against infection by HIV or for treating AIDS or ARC. Preferred combinations are simultaneous or alternating treatments of a compound of the present invention and a protease inhibitor (e.g., indinavir, nelfinavir, ritonavir, saquinavir and others), a reverse transcriptase inhibitor [nucleoside (e.g., AZT, 3TC, ddC, ddI, d4T, abacavir and others, and/or non-nucleoside (e.g., efavirenz, nevirapine, and others), or some combination of two or more of these inhibitors (see Table above). A few representative examples of relevant patents citing combinations are: EPO 0,484,071, U.S. Pat. No. 5,413,999, WO 9962513.

In such combinations the compound of the present invention and other active agents may be separately administered or concurrently administered. In addition, the administration of one element may be prior to, concurrent to, or subsequent to the administration of other agent(s).

The following representative examples are provided to illustrate details for the preparation of the compounds of the present invention. The examples are not intended to be limitations on the scope of the present invention and they should not be so construed. Furthermore, the compounds described in the following examples are not to be viewed as forming the only set of compounds that is considered as the invention, and any combination of components of the compounds or their moieties may itself form a set. This has been addressed previously in this patent document. Those skilled in the art will readily comprehend that known variations of reaction conditions and synthetic conversions described in the following preparative procedures can be used to prepare these other compounds.

Chemical Synthesis

Chemical schemes for representative examples 1 through 12 are Schemes 1 and 2 shown below.

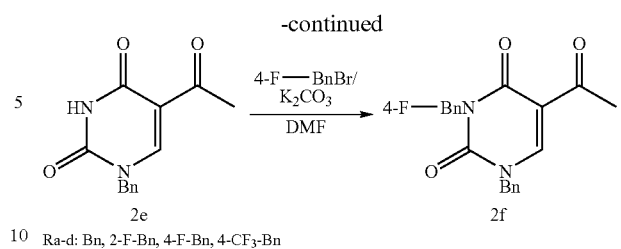

Ra-d: Bn, 2-F-Bn, 4-F-Bn, 4-CF$_3$-Bn

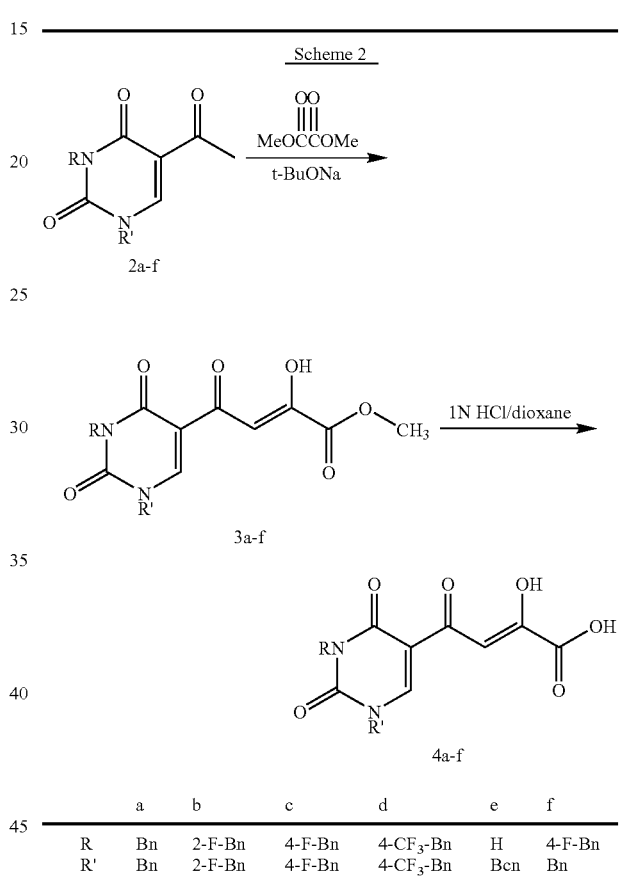

| | a | b | c | d | e | f |
|---|---|---|---|---|---|---|
| R | Bn | 2-F-Bn | 4-F-Bn | 4-CF$_3$-Bn | H | 4-F-Bn |
| R' | Bn | 2-F-Bn | 4-F-Bn | 4-CF$_3$-Bn | Bcn | Bn |

REPRESENTATIVE EXAMPLE 1

Methyl 4-(1,3-dibenzyl-1,2,3,4-tetrahydro-2,4-dioxopyrimidin-5-yl)-2-hydroxy-4-oxobut-2-enoate (3a)

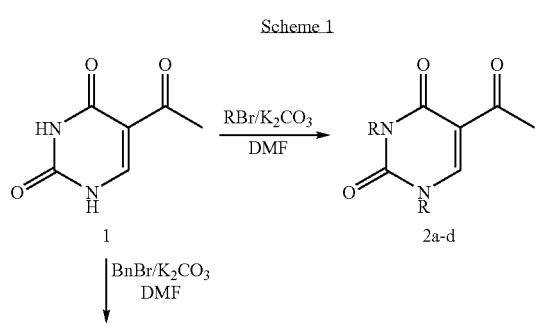

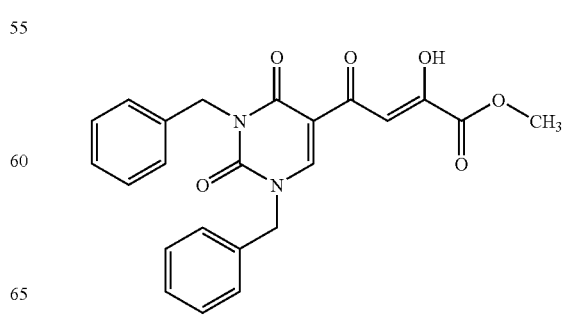

Step 1

Preparation of 5-acetyl-1,3-dibenzyluracil (2a)

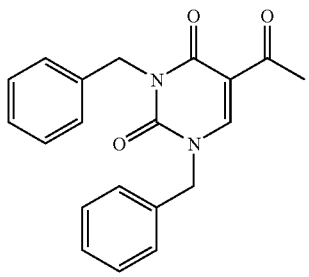

A suspension of 5-acetyluracil (3.1 g, 20 mmol), and potassium carbonate (6.9 g, 50 mmol) in DMF (75 ml) was stirred for 20 min. Then benzyl bromide (6.0 ml, 50 mmol) was added. The resulting mixture was stirred for 8 h at room temperature. DMF was distilled under vacuum. The residue was purified by column (dichloromethane:methanol 40:1). The appropriate fraction was concentrated and crystallized from ethanol to afford 5.34 g of a white solid. Yield was 79.8%. Mp. 92-93° C. $^1$HNMR (CDCl$_3$): 8.23 (s, 1H), 7.29-7.49 (m, 10H), 5.17 (s, 2H), 5.01 (s, 2H), 2.62 (s, 3H). $^{13}$CNMR (CDCl$_3$): 194.5, 160.7, 151.0, 148.4, 136.2, 134.4, 129.2, 129.0, 128.9, 128.5, 128.2, 127.8, 112.2, 53.4, 44.9, 30.7. FAB-HRMS: [M+H]$^+$ Calcd. for C$_{20}$H$_{19}$N$_2$O$_3$ 335.1396. Found 335.1412.

Step 2

Preparation of methyl 4-(1,3-dibenzyl-1,2,3,4-tetrahydro-2,4-dioxopyrimidin-5-yl)-2-hydroxy-4-oxobut-2-enoate (3a)

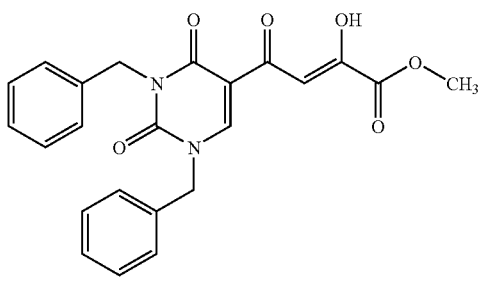

To a stirred solution of sodium t-butoxide (577 mg, 6 mmol) in anhydrous THF (15 ml) at room temperature was added, dropwise, dimethyl oxalate (472 mg, 4 mmol) in THF (7 ml) followed by 5-acetyl-1,3-dibenzyluracil (2a) (669 mg, 2 mmol) in THF (8 ml). The resulting mixture was stirred at room temperature for 4 h and then was acidified to pH=2. THF was evaporated. The residue in CH$_2$Cl$_2$ (100 ml) washed with brine (20 ml) and purified by column chromatography (hexane:ethyl acetate, 2:1). The appropriate fraction was concentrated and crystallized from ethanol to give 254 mg of a yellow solid. Yield was 29.1%. Mp. 158-159° C. $^1$HNMR (CDCl$_3$): 15.04 (s, br, 1H), 8.36 (s, 1H), 7.72 (s, 1H), 7.29-7.49 (m, 10H), 5.18 (s, 2H), 5.05 (s, 2H), 3.92 (s, 3H). $^{13}$CNMR (CDCl$_3$): 185.7, 168.8, 162.4, 159.7, 150.5, 148.5, 136.0, 134.0, 129.4, 129.1, 129.0, 128.5, 128.3, 127.9, 109.0, 101.6, 53.7, 53.2, 45.0. FAB-HRMS: [M+H]$^+$ Calcd. for C$_{23}$H$_{21}$N$_2$O$_6$ 421.1400. Found 421.1418.

REPRESENTATIVE EXAMPLE 2

4-(1,3-Dibenzyl-1,2,3,4-tetrahydro-2,4-dioxopyrimidin-5-yl)-2-hydroxy-4-oxobut-2-enoic acid (4a)

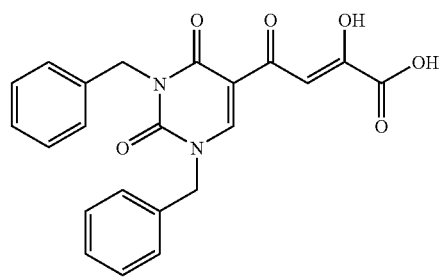

A solution of methyl 4-(1,3-dibenzyl-1,2,3,4-tetrahydro-2,4-dioxopyrimidin-5-yl)-2-hydroxy-4-oxobut-2-enoate (3a) (757 mg, 1.8 mmol) in dioxane (100 ml) was refluxed with 1N HCl (60 ml) for 4 h. The solution was evaporated to dryness. The resulting solid vas recrystallized from hexane and ethyl acetate (3:1) to give 617 mg a pale yellow solid. Yield as 84.2%. Mp. 186-188° C. $^1$HNMR (DMSO-d6): 8.89 (s, 1H), 7.57 (s, 1H), 7.24-7.36 (m, 10H), 5.16 (s, 2H), 5.02 (s, 2H). $^{13}$CNMR (DMSO-d$_6$): 186.1, 169.0, 163.2, 159.9, 151.1, 150.2, 136.5, 135.8, 128.7, 128.4, 128.0, 127.8, 127.6, 127.3, 107.7, 100.9, 52.8, 44.2. FAB-HRMS: [M+H]$^+$ Calcd. for C$_{22}$H$_{19}$N$_2$O$_6$ 407.1243. Found 407.1248.

REPRESENTATIVE EXAMPLE 3

Methyl 4-[1,3-bis(2-fluorobenzyl)-1,2,3,4-tetrahydro-2,4-dioxopyrimidin-5-yl]-2-hydroxy-4-oxobut-2-enoate (3b)

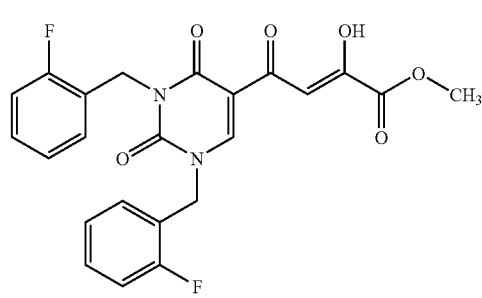

Step 1

Preparation of 1,3-bis(2-fluorobenzyl)-5-acetyluracil (2b)

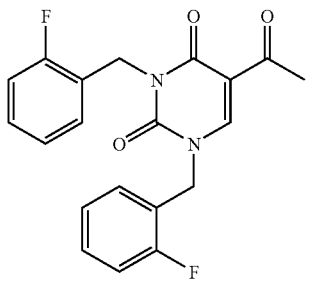

The title compound for this step was synthesized using a similar procedure to that described in Example 1, step 1, except that benzyl bromide was replaced with 2-fluorobenzyl bromide. The yield was 43.9%. Mp. 149-150° C. $^1$HNMR (CDCl$_3$): 8.35 (d, 1H, J=1.0 Hz), 7.36-7.44 (m, 2H), 7.04-7.26 (m, 6H), 5.24 (s, 2H), 5.07 (s, 2H), 2.62 (s, 3H). $^{13}$CNMR (CDCl$_3$): 194.3, 161.1 (d, J=247.9 Hz), 160.7 (d, J=247.9 Hz), 160.6, 150.8, 148.8 (d, J=2.9 Hz), 131.3 (d, J=3.4 Hz), 130.9 (d, J=8.2 Hz), 129.19 (d, J=8.2 Hz), 129.17 (d, J=2.9 Hz), 124.7 (d, J=3.8 Hz), 124.1 (d, J=3.8 Hz), 123.1 (d, J=14.5 Hz), 121.4 (d, J=14.5 Hz), 115.9 (d, J=21.6 Hz), 115.5 (d, J=21.6 Hz), 112.2, 47.8, 38.8, 30.6.

FAB-HRMS: [M+H]$^+$ Calcd. for C$_{20}$H$_{17}$F$_2$N$_2$O$_3$ 371.1207. Found 371.1202.

Step 2

Preparation of methyl 4-[1,3-bis(2-fluorobenzyl)-1,2,3,4-tetrahydro-2,4-dioxopyrimidin-5-yl]-2-hydroxy-4-oxobut-2-enoate (3b)

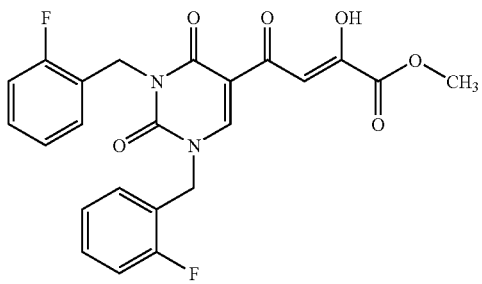

The title compound for this step was synthesized using a similar procedure to that described in the Example 1, step 2, except that 5-acetyl-1,3-dibenzyluracil was replaced with 1,3-bis(2-fluorobenzyl)-5-acetyluracil. The title compound was crystallized from the mixture of hexane and ethyl acetate (3:1) and obtained in 21.1% yield. Mp. 158-160° C. $^1$HNMR (CDCl$_3$): 15.06 (br, s, 1H), 8.52 (s, 1H), 7.69 (s, 1H), 7.38-7.46 (m, 2H), 7.04-7.26 (m, 6H), 5.25 (s, 2H), 5.11 (s, 2H), 3.90 (s, 3H). $^{13}$CNMR (CDCl$_3$): 185.3, 169.2, 162.4, 161.2 (d, J=247.3 Hz), 160.7 (d, J=247.9 Hz), 159.6, 150.3, 148.9 (d, J=3.4 Hz), 131.5 (d, J=3.4 Hz), 131.2 (d, J=8.7 Hz), 129.3 (d, J=8.2 Hz), 129.2 (d, J=3.4 Hz), 124.8 (d, J=3.8 Hz), 124.1 (d, J=3.9 Hz), 122.8 (d, J=14.5 Hz), 121.2 (d, J=14.3 Hz), 116.0 (d, J=21.1 Hz), 115.6 (d, J=21.6 Hz), 108.9, 101.5, 53.0, 48.2 (d, J=3.4 Hz), 38.9 (d, J=4.8 Hz). FAB-HRMS: [M+H]$^+$ Calcd. for C$_{23}$H$_{19}$F$_2$N$_2$O$_6$ 457.1211. Found 457.1203.

REPRESENTATIVE EXAMPLE 4

4-[1,3-Bis(2-fluorobenzyl)-1,2,3,4-tetrahydro-2,4-dioxopyrimidin-5-yl]-2-hydroxy-4-oxobut-2-enoic acid (4b)

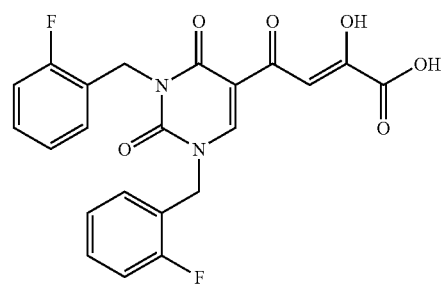

The title compound was synthesized using a similar procedure to that described in Example 2, except that methyl 4-(1,3-dibenzyl-1,2,3,4-tetrahydro-2,4-dioxopyrimidin-5-yl)-2-hydroxy-4-oxobut-2-enoate was replaced with methyl 4-[1,3-bis(2-fluorobenzyl)-1,2,3,4-tetrahydro-2,4-dioxopyrimidin-5-yl]-2-hydroxy-4-oxobut-2-enoate (3b). The title compound was crystallized from hexane and ethyl acetate (2:1) to give an off-white solid. The yield was 56.5%. Mp. 178-179° C. $^1$H NMR (DMSO-d6): 15.00 (br, s, 1H), 14.02 (br, s, 1H), 8.90 (s, 1H), 7.55 (s, 1H), 7.08-7.40 (m, 8H), 5.23 (s, 2H), 5.05 (s, 2H). $^{13}$CNMR (DMSO-d6): 185.7, 169.2, 163.0, 160.2 (d, J=246.0 Hz), 159.8 (d, J=244.6 Hz), 159.7, 151.2, 149.9, 130.2, 129.0 (d, J=8.2 Hz), 128.4 (d, J=3.9 Hz), 124.5 (d, J=3.3 Hz), 124.3 (d, J=3.3 Hz), 123.1 (d, J=13.9 Hz), 122.3 (d, J=14.5 Hz), 115.4 (d, J=21.1 Hz), 115.1 (d, J=21.1 Hz), 107.6, 100.7, 47.8 (d, J=3.4 Hz), 38.2 (d, J=4.8 Hz).

FAB-HRMS: [M+H]$^+$ Calcd. for C$_{22}$H$_{17}$F$_2$N$_2$O$_6$ 443.1055. Found 443.1045.

REPRESENTATIVE EXAMPLE 5

Methyl 4-[1,3-bis(4-fluorobenzyl)-1,2,3,4-tetrahydro-2,4-dioxopyrimidin-5-yl]-2-hydroxy-4-oxobut-2-enoate (3c)

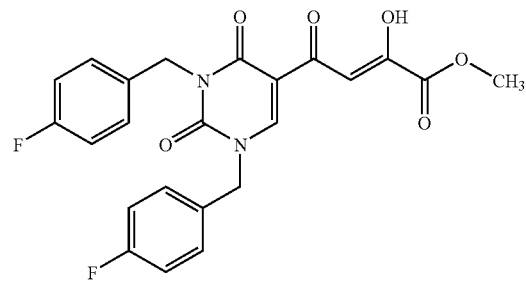

Step 1

1,3-bis(4-fluorobenzyl)-5-acetyluracil (2c)

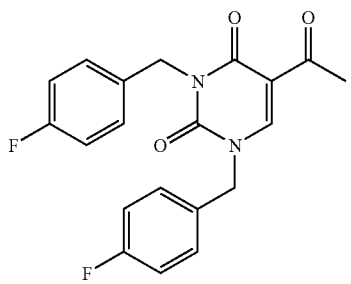

The title compound was synthesized using a similar procedure to that described in Example 1, step 1, except that benzyl bromide was replaced with 4-fluorobenzyl bromide. The yield was 51.8%. Mp. 134-135° C. $^1$HNMR (CDCl$_3$): 8.22 (s, 1H), 7.48 (dd, 2H, J=9.0. 5.5 Hz), 7.32 (dd, 2H, J=8.5, 5.0 Hz), 6.99-7.09 (m, 4H), 5.11 (s, 2H), 4.97 (s, 2H), 2.62 (s, 3H). $^{13}$CNMR (CDCl$_3$): 194.3, 163.0 (d, J=248.3 Hz), 162.4 (d, J=246.4 Hz), 160.6, 150.9. 148.2, 132.1 (d, J=3.4 Hz), 131.1 (d, J=8.2 Hz), 130.23 (d, J=8.5 Hz), 130.26 (d, J=2.9 Hz), 116.2 (d, J=21.4 Hz), 115.3 (d, J=21.5 Hz), 112.4, 52.9, 44.2, 30.6. FAB-HRMS: [M+H]$^+$ Calcd. for C$_{20}$H$_{17}$F$_2$N$_2$O$_3$ 371.1207. Found 371.1220.

Step 2

Preparation of methyl 4-[1,3-bis(4-fluorobenzyl)-1,2,3,4-tetrahydro-2,4-dioxopyrimidin-5-yl]-2-hydroxy-4-oxobut-2-enoate (3c)

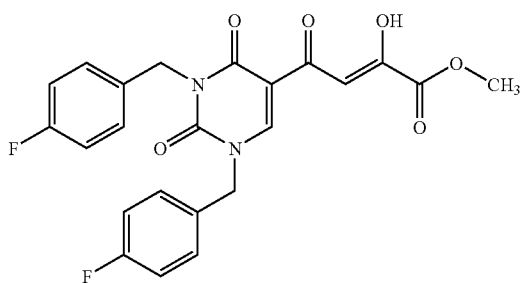

The title compound was synthesized using a similar procedure to that described in Example 1, step 2, except that 5-acetyl-1,3-dibenzyluracil was replaced with 1,3-bis(4-fluorobenzyl)-5-acetyluracil. The title compound was recrystallized from ethanol and obtained in 23.5% yield. Mp. 171-173° C. $^1$HNMR (CDCl$_3$): 15.02 (br, s, 1H), 8.35 (s, 1H), 7.71 (s, 1H), 7.49 (m, 2H), 7.34 (m, 2H), 7.09 (m, 2H), 7.00 (m, 2H), 5.13 (s, 2H), 5.02 (s, 2H), 3.92 (s, 3H). $^{13}$CNMR (CDCl$_3$): 185.3, 169.2, 163.1 (d, J=248.8 Hz), 162.5 (d, J=246.4 Hz), 162.4, 159.6, 150.5, 148.2, 131.8 (d, J=3.4 Hz), 131.2 (d, J=8.2 Hz), 130.3 (d, J=8.7 Hz), 129.9 (d, J=3.4 Hz), 116.4 (d, J=21.6 Hz), 115.4 (d, J=21.6 Hz), 109.2, 101.5, 53.14, 53.12, 44.3. FAB-HRMS: [M+H]$^+$ Calcd. for C$_{23}$H$_{19}$F$_2$N$_2$O$_6$ 457.1211. Found 457.1196.

REPRESENTATIVE EXAMPLE 6

4-[1,3-Bis(4-fluorobenzyl)-1,2,3,4-tetrahydro-2,4-dioxopyrimidin-5-yl]-2-hydroxy-4-oxobut-2-enoic acid (4c)

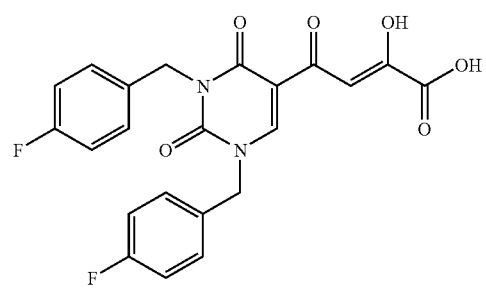

The title compound was synthesized using a similar procedure to that described in Example 2, except that methyl 4-(1,3-dibenzyl-1,2,3,4-tetrahydro-2,4-dioxopyrimidin-5-yl)-2-hydroxy-4-oxobut-2-enoate was replaced with methyl 4-[1,3-bis(4-fluorobenzyl)-1,2,3,4-tetrahydro-2,4-dioxopyrimidin-5-yl]-2-hydroxy-4-oxobut-2-enoate (3c). The title compound was crystallized from hexane and ethyl acetate (3:1). The yield was 49.7%. Mp. 186-188° C. $^1$HNMR (DMSO-d$_6$): 15.07 (br, s, 1H), 14.02 (br, s, 1H), 8.90 (s, 1H), 7.56 (s, 1H), 7.34-7.46 (m, 4H), 7.10-7.21 (m, 4H), 5.13 (s, 2H), 4.98 (s, 2H). $^{13}$CNMR (DMSO-d$_6$): 185.8, 169.2, 163.1, 161.8 (d, J=244.1 Hz), 161.3 (d, J=243.2 Hz), 159.7, 150.8, 150.1, 132.6 (d, J=2.9 Hz), 131.8 (d, J=3.4 Hz), 130.2 (d, J=8.2 Hz), 129.9 (d, J=8.2 Hz), 115.4 (d, J=21.6 Hz), 115.0 (d, J=21.0 Hz), 107.7, 100.7, 52.1, 43.5. FAB-HRMS: [M+H]$^+$ Calcd. for C$_{22}$H$_{17}$F$_2$N$_2$O$_6$ 443.1055. Found 443.1044.

REPRESENTATIVE EXAMPLE 7

Methyl 4-[1,3-bis(4-(trifluoromethyl)benzyl)-1,2,3,4-tetrahydro-2,4-dioxopyrimidin-5-yl]-2-hydroxy-4-oxobut-2-enoate (3d)

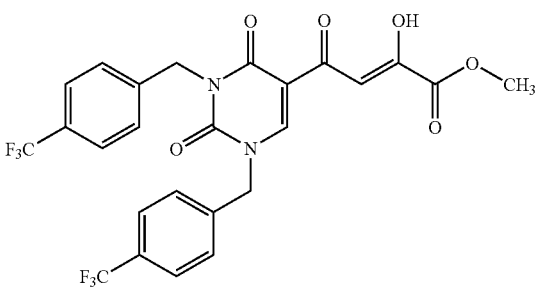

Step 1

Preparation of 1,3-bis(4-(trifluoromethyl)benzyl)-5-acetyluracil (2d)

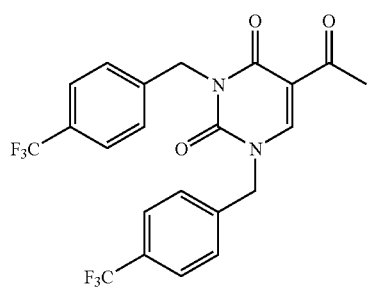

The title compound was synthesized using a similar to that described in the Example 1, step 1, except that benzyl bromide was replaced with 4-(trifluoromethyl)benzyl bromide. The yield was 65.1%, amorphous solid. $^1$HNMR (CDCl$_3$): 8.27 (s, 1H), 7.44-7.66 (m, 8H), 5.20 (s, 2H), 5.07 (s, 2H), 2.63 (s, 3H). $^{13}$CNMR (CDCl$_3$): 194.1, 160.5, 150.9, 148.3, 140.0, 138.2, 131.3 (q, J=32.7 Hz), 130.2 (q, J=32.7 Hz), 129.3, 128.4, 126.3 (q, J=3.8 Hz), 125.5 (q, J=3.8 Hz), 124.0 (q, J=272.0 Hz), 123.7 (q, J=272.3 Hz), 112.6, 53.2, 44.5, 30.6. FAB-HRMS: [M+]$^+$ Calcd. for C$_{22}$H$_{17}$F$_6$N$_2$O$_3$ 471.1143. Found 471.1148.

Step 2

Preparation of methyl 4-[1,3-bis(4-(trifluoromethyl)benzyl)-1,2,3,4-tetrahydro-2,4-dioxopyrimidin-5-yl]-2-hydroxy-4-oxobut-2-enoate (3d)

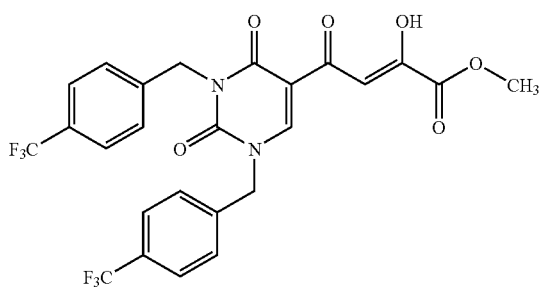

The title compound was synthesized using a similar procedure to that described in Example 1, step 2, except that 5-acetyl-1,3-dibenzyluracil was replaced with 1,3-bis(4-(trifluoromethyl)benzyl)-5-acetyluracil. The title compound crystallized from a mixture of hexane and ethyl acetate (3:1) and ethanol and was obtained in 20.3% yield. Mp. 189-191° C. $^1$H NMR (CDCl$_3$): 14.98 (br, s, 1H), 8.41 (s, 1H), 7.70 (s, 1H), 7.46-7.68 (m, 8H), 5.21 (s, 2H), 5.11 (s, 2H). $^{13}$C NMR (CDCl$_3$): 185.0, 169.5, 162.3, 159.5, 150.4, 148.3, 139.7, 138.0, 131.4 (q, J=32.5 Hz), 130.3 (q, J=32.4 Hz), 129.4, 128.5, 126.3 (q, J=3.7 Hz), 125.5 (q, J=3.7 Hz), 124.0 (q, J=271.9 Hz), 123.7 (q, J=272.3 Hz), 109.4, 101.5, 53.4, 53.2, 44.6. FAB-HRMS: [M+H]$^+$ Calcd. for C$_{25}$H$_{19}$F$_6$N$_2$O$_6$ 557.1147. Found 557.1135.

REPRESENTATIVE EXAMPLE 8

4-[1,3-Bis(4-(trifluoromethyl)benzyl)-1,2,3,4-tetrahydro-2,4-dioxopyrimidin-5-yl]-2-hydroxy-4-oxobut-2-enoic acid (4d)

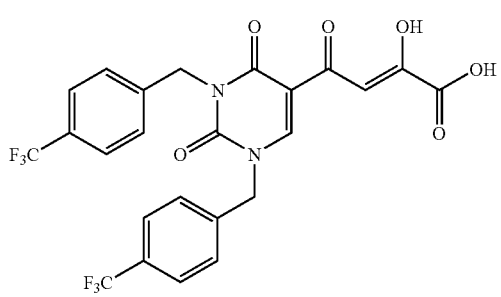

The title compound was synthesized using a similar procedure to that described in Example 2, except that methyl 4-(1,3-dibenzyl-1,2,3,4-tetrahydro-2,4-dioxopyrimidin-5-yl)-2-hydroxy-4-oxobut-2-enoate was replaced with methyl 4-[1,3-bis(4-(trifluoromethyl)benzyl)-1,2,3,4-tetrahydro-2,4-dioxopyrimidin-5-yl]-2-hydroxy-4-oxobut-2-enoate (3d). The title compound was recrystallized from hexane and ethyl acetate (3:1). The yield was 68.2%. Mp. 176-178° C. $^1$HNMR (DMSO-d$_6$): 14.98 (br, s, 1H), 14.02 (br, s, 1H), 8.99 (s, 1H), 7.72 (d, 2H, J=8.0 Hz), 7.66 (d, 2H, J=8.5 Hz), 7.59 (d, 2H, J=8.5 Hz), 7.57 (s, 1H), 7.51 (d, 2H, J=8.0 Hz), 5.26 (s, 2H), 5.09 (s, 2H). $^{13}$CNMR (DMSO-d$_6$): 185.8, 169.3, 163.1, 159.9, 151.3, 150.2, 141.2, 140.5, 128.4 (q, J=31.5 Hz), 128.3, 128.2, 127.9 (q, J=31.7 Hz), 125.4 (q, J=3.8 Hz), 125.2 (q, J=3.8 Hz), 124.2 (q, J=272.3 Hz), 124.1 (q, J=271.8 Hz), 108.0, 100.7, 52.6, 43.9. FAB-HRMS: [M+H]$^+$ Calcd. for C$_{24}$H$_{17}$F$_6$N$_2$O$_6$ 543.0991. Found 543.1003.

REPRESENTATIVE EXAMPLE 9

Methyl 4-(1-benzyl-1,2,3,4-tetrahydro-2,4-dioxopyrimidin-5-yl)-2-hydroxy-4-oxobut-2-enoate (3e)

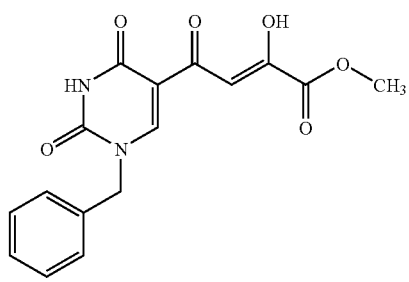

31

Step 1

Preparation of 5-acetyl-1-benzyluracil (2e)

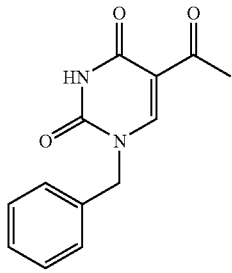

The title compound was synthesized in 69.9% yield by a similar procedure to that described for Example 1, step 1, but using 1.1 equiv of benzyl bromide and 1.0 equiv of potassium carbonate in DMF. Mp. 196-197° C. $^1$HNMR (DMSO-$d_6$): 11.69 (br, s, 1H), 8.54 (s, 1H), 7.30-7.36 (m, 5H), 5.03 (s, 2H), 2.44 (s, 3H). $^{13}$CNMR (DMSO-$d_6$): 193.5, 161.6, 151.5, 150.3, 136.2, 128.7, 127.9, 127.7, 111.8, 51.1, 30.3. FAB-HRMS: [M+H]$^+$ Calcd. for $C_{13}H_{13}N_2O_3$ 245.0926. Found 245.0932.

Step 2

Preparation of methyl 4-(1-benzyl-1,2,3,4-tetrahydro-2,4-dioxopyrimidin-5-yl)-2-hydroxy-4-oxobut-2-enoate (3e)

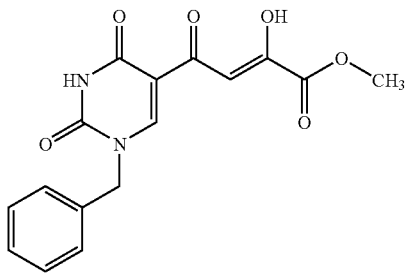

The title compound was synthesized using a similar procedure to that described in Example 1, step 2, except that 5-acetyl-1,3-dibenzyluracil was replaced with 5-acetyl-1-benzyluracil. The title compound was crystallized from ethanol and obtained in 77.2% yield. Mp. 197-199° C. $^1$HNMR (DMSO-$d_6$): 11.90 (s, 1H), 8.82 (s, 1H), 7.57 (s, 1H), 7.31-7.37 (m, 5H), 5.08 (s, 2H), 3.82 (s, 3H). $^{13}$CNMR (DMSO-$d_6$): 185.9, 167.8, 162.2, 161.0, 152.7, 149.8, 135.9, 128.7, 127.9, 127.7, 107.9, 100.9, 53.0, 51.5. FAB-HRMS: [M+H]$^+$ Calcd. for $C_{16}H_{15}N_2O_6$ 331.0930. Found 331.0928.

32

REPRESENTATIVE EXAMPLE 10

4-(1-Benzyl-1,2,3,4-tetrahydro-2,4-dioxopyrimidin-5-yl)-2-hydroxy-4-oxobut-2-enoic acid (4e)

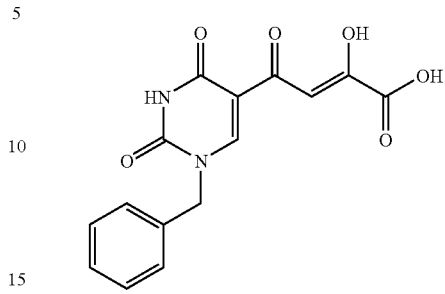

The title compound was synthesized using a similar procedure to that described in Example 2, replacing methyl 4-(1,3-dibenzyl-1,2,3,4-tetrahydro-2,4-dioxopyrimidin-5-yl)-2-hydroxy-4-oxobut-2-enoate with methyl 4-(1-benzyl-1,2,3,4-tetrahydro-2,4-dioxopyrimidin-5-yl)-2-hydroxy-4-oxobut-2-enoate (3e). The title compound was crystallized from mixture of tetrahydrofuran and chloroform (2:3). The yield was 79.7%. Mp. 195-197° C. $^1$HNMR (DMSO-$d_6$): 15.10 (br, s, 1H), 13.97 (br, s, 1H), 11.87 (s, 1H), 8.79 (s, 1H), 7.54 (s, 1H), 7.30-7.36 (m, 5H), 5.08 (s, 2H). $^{13}$CNMR (DMSO-$d_6$): 186.0, 169.2, 163.2, 161.0, 152.5, 149.9, 136.0, 128.7, 127.9, 127.7, 108.2, 100.8, 51.5. FAB-HRMS: [M+H]$^+$ Calcd. for $C_{15}H_{13}N_2O_6$ 317.0774. Found 317.0769.

REPRESENTATIVE EXAMPLE 11

Methyl 4-[3-(4-fluorobenzyl)-1-benzyl-1,2,3,4-tetrahydro-2,4-dioxopyrimidin-5-yl]-2-hydroxy-4-oxobut-2-enoate (3f)

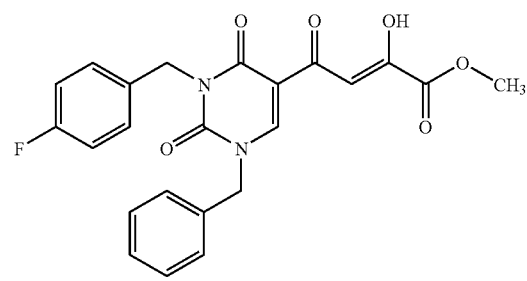

Step 1

Preparation of 3-(4-fluorobenzyl)-5-acetyl-1-benzyluracil (2f)

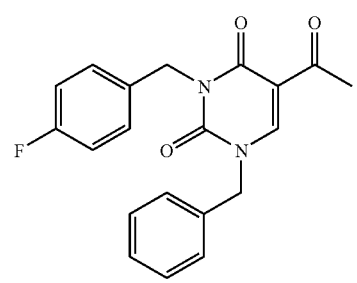

The title compound was synthesized in 93.7% yield by benzylation of 5-acetyl-1-benzyluracil (2e) with 2 equiv of 4-fluorobenzyl bromide and 2 equiv of potassium carbonate in DMF. Mp. 106-108° C. $^1$HNMR (CDCl$_3$): 8.23 (s, 1H), 7.30-7.50 (m, 7H), 7.00 (m, 2H), 5.12 (s, 2H), 5.01 (s, 2H), 2.61 (s, 3H). $^{13}$CNMR (CDCl$_3$): 194.3, 162.4 (d, J=246.4 Hz), 160.7, 151.0, 148.4, 134.4, 132.1 (d, J=3.4 Hz), 131.1 (d, J=8.2 Hz), 129.2, 128.9, 128.2, 115.3 (d, J=21.6 Hz), 112.3, 53.4, 44.2, 30.6. FAB-HRMS: [M+H]$^+$ Calcd. for C$_{20}$H$_{18}$FN$_2$O$_3$ 353.1301. Found 353.1310.

Step 2

Preparation of methyl 4-[3-(4-fluorobenzyl)-1-benzyl-1,2,3,4-tetrahydro-2,4-dioxopyrimidin-5-yl]-2-hydroxy-4-oxobut-2-enoate (3f)

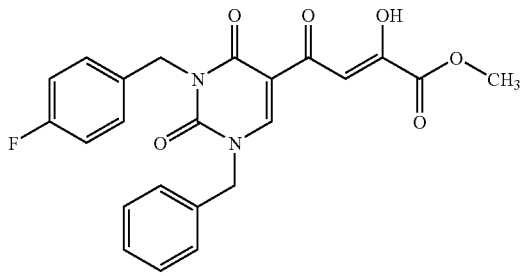

The title compound was synthesized using a similar procedure to that described Example 1, step 2, replacing 5-acetyl-1,3-dibenzyluracil with 3-(4-fluorobenzyl)-5-acetyl-1-benzyluracil. The title compound was crystallized from ethanol and obtained in 30.5% yield. Mp. 165-167° C. $^1$HNMR (CDCl$_3$): 15.04 (br, s, 1H), 8.36 (s, 1H), 7.72 (s, 1H), 7.28-7.52 (m, 7H), 7.01 (t, 2H, J=8.5 Hz), 5.15 (s, 2H), 5.06 (s, 2H), 3.93 (s, 3H). $^{13}$CNMR (CDCl$_3$): 185.4, 169.2, 162.5 (d, J=246.8 Hz), 162.4, 159.7, 150.5, 148.4, 134.1, 131.9 (d, J=3.4 Hz), 131.2 (d, J=8.2 Hz), 129.4, 129.1, 128.3, 115.4 (d, J=21.6 Hz), 109.1, 101.5, 53.7, 53.1, 44.3. FAB-HRMS: [M+H]$^+$ Calcd. for C$_{23}$H$_{20}$FN$_2$O$_6$ 439.1305. Found 439.1294.

REPRESENTATIVE EXAMPLE 12

4-[3-(4-Fluorobenzyl)-1-benzyl-1,2,3,4-tetrahydro-2,4-dioxopyrimidin-5-yl]-2-hydroxy-4-oxobut-2-enoic acid (4f)

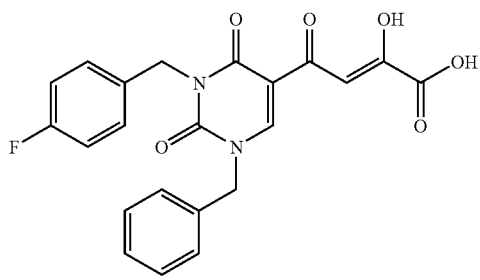

The title compound was synthesized using a similar procedure to that described in Example 2, replacing methyl 4-(1,3-dibenzyl-1,2,3,4-tetrahydro-2,4-dioxopyrimidin-5-yl)-2-hydroxy-4-oxobut-2-enoate with methyl 4-[3-(4-fluorobenzyl)-1-benzyl-1,2,3,4-tetrahydro-2,4-dioxopyrimidin-5-yl]-2-hydroxy-4-oxobut-2-enoate (3f). The title compound was crystallized from a mixture of hexane and ethyl acetate (2:1). The yield was 64.0%. Mp. 188-190° C. $^1$HNMR (DMSO-d$_6$): 15.05 (br, s, 1H), 14.01 (br, s, 1H), 8.87 (s, 1H), 7.56 (s, 1H), 7.30-7.37 (m, 7H), 7.12 (m, 2H), 5.15 (s, 2H), 4.99 (s, 2H). $^{13}$CNMR (DMSO-d$_6$): 185.7, 169.2, 163.1, 161.4 (d, J=243.0 Hz), 159.7, 150.8, 150.1, 135.6, 132.6 (d, J=3.4 Hz), 129.9 (d, J=8.2 Hz), 128.6, 127.9, 127.7, 115.5 (d, J=21.6 Hz), 107.7, 100.7, 52.7, 43.5. FAB-HRMS: [M+H]$^+$ Calcd. for C$_{22}$H$_{18}$FN$_2$O$_6$ 425.1149. Found 425.1156.

REPRESENTATIVE EXAMPLE 13

4-(9-Benzyl-9H-purin-6-yl)-2-hydroxy-4-oxo-but-3-enoic acid (11)

The relevant scheme is Scheme 3 shown below.

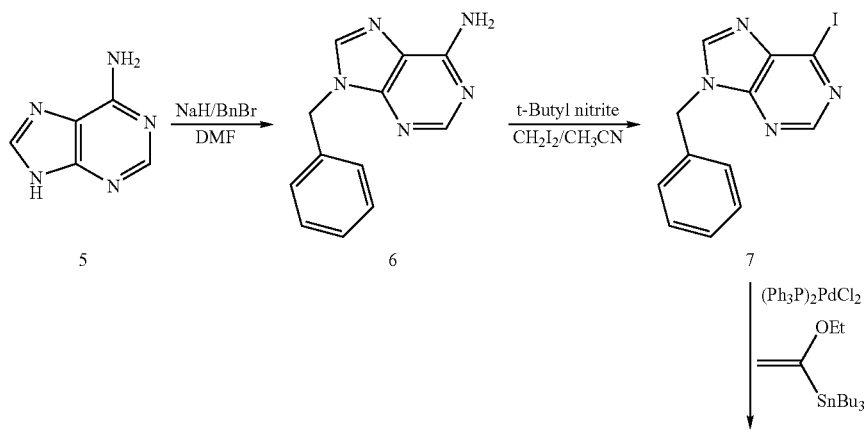

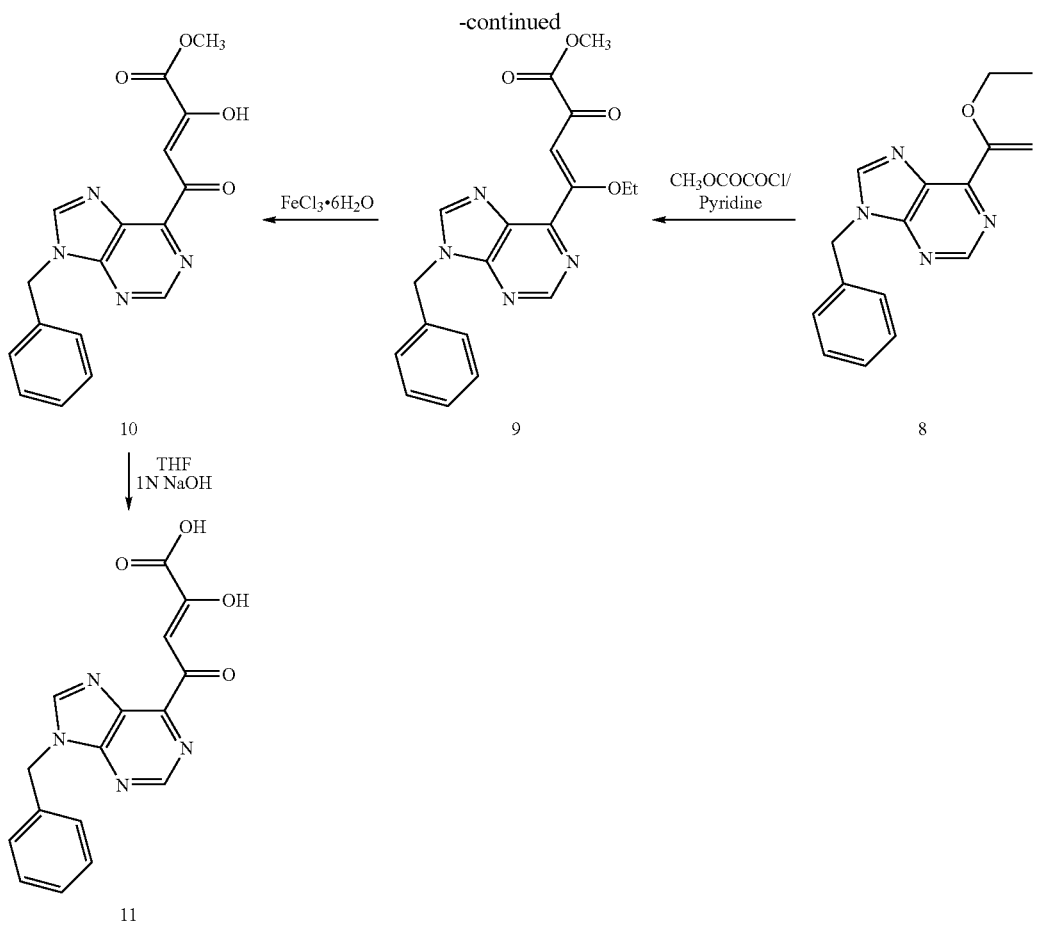

Step 1

9-Benzyladenine (6)

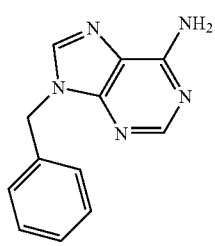

To a suspension of adenine (5) (5.00 g, 37.0 mmol) in dry DMF (120 mL) was added NaH (1.77 g, 44.4 mmol) at room temperature. The reaction mixture was stirred for 30 min and the resulting white suspension was warmed to 60° C. for an additional 30 min. Benzyl bromide (7.59 g, 44.4 mmol) was added and the mixture was stirred for 24 h at 60° C. TLC of the reaction mixture indicated the formation of two products. DMF was distilled off under reduced pressure and the resulting residue was treated with water (20 mL). The white solid that separated out, was filtered and dried under vacuum. Separation and purification was through flash column chromatography using $CHCl_3$:MeOH (9:1) for elution. 9-Benzyladenine: yield 5.5 g. (66%); mp 231-232° C.; $^1$H NMR (DMSO-$d_6$): δ 5.38 (s, 2H, $CH_2$), 7.29-7.33 (m, 7H, Ar—H and $NH_2$), 8.17 (s, 1H, purine $C_8$—H), 8.28 (s, 1H, purine $C_2$—H). 7-Benzyladenine: yield 1.8 g. (21%). Mp 252-255° C. $^1$H NMR (DMSO-$d_6$): δ 5.53 (s, 2H, $CH_2$), 7.29-7.48 (m, 5H, Ar—H), 7.81 (s, 1H, purine $C_8$—H), 8.0-8.1 (br, 2H, $NH_2$), 8.6 (s, 1H, purine $C_2$—H).

Step 2

9-Benzyl-6-iodopurine (7)

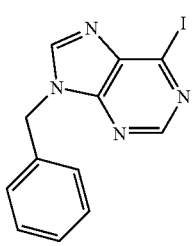

To a stirred suspension of 9-benzyladenine (6) (1.00 g, 4.4 mmol) in anhydrous acetonitrile (50 mL), was added diidomethane (5.82 g, 21.7 mmol) followed by t-butyl nitrite (2.24 g, 21.7 mmol) at 0-5° C. (ice bath). While maintaining the cooling, the solution was purged with nitrogen for 30 min. The ice bath was removed and the reaction mixture was heated under an atmosphere of nitrogen at 60-65° C. for 5 h. Acetonitrile and the excess reagents were distilled off and the residue obtained redissolved in chloroform (100 mL) and washed with saturated aqueous sodium sulfite (2×50 mL) followed by brine solution (2×50 mL). The chloroform layer was dried over anhydrous sodium sulfate and concentrated to give a reddish oil which was purified by flash chromatography on silica gel using EtOAc/hexane (3:7) for elution. Yield: 0.519 g. (34%). Mp 152-153° C. $^1$H NMR (DMSO-$d_6$): δ 5.51 (s, 2H, $CH_2$), 7.31-7.36 (m, 5H-1, Ar—H), 8.65 (s, 1H, purine $C_2$—H), 8.83 (s, 1H, purine $C_2$—H). $^{13}$C NMR (DMSO-$d_6$): δ 47.4, 123.2, 128.1, 128.1, 128.4, 129.2, 136.5, 138.4, 146.9, 148.3, 152.4.

Step 3
9-Benzyl-6-(α-ethoxyvinyl)purine (8)

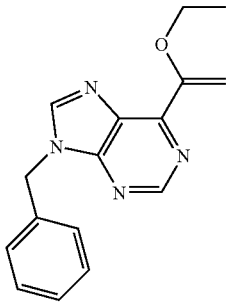

A mixture of 9-benzyl-6-iodopurine (7) (1.00 g, 2.8 mmol), bis(triphenylphosphine)-palladium(II) chloride (0.208 g, 0.02 mmol) and ethoxyvinyl(tributyl)tin (2.07 g, 3.8 mmol) in dry DMF (4 mL) was heated under $N_2$ at 100° C. for 6 h. TLC indicated completion of reaction. DMF was distilled off under reduced pressure and the resulting residue was redissolved in EtOAc (50 mL) and filtered through a pad of celite. The solvent (EtOAc) was distilled off and the residue obtained purified by flash chromatography. Yield 0.393 g, (47%). Mp 114-115° C. $^1$H NMR ($CDCl_3$): δ 1.55 (t, 3H, $CH_3$, J=7.5 Hz), 4.13 (q, 2H, $CH_2$, J=13.7 Hz), 4.99 (d, 1H, CH, J=3 Hz), 5.48 (s, 2H, benzylic $CH_2$), 6.16 (d, 1H, CH, J=3 Hz), 7.30-7.38 (m, 5H, Ar—H), 8.09 (s, 1H, purine $C_8$—H), 9.07 (s, 1H, purine $C_2$—H). $^{13}$C NMR ($CDCl_3$): δ14.3, 47.3, 63.7, 94.7, 127.8, 127.8, 128.6, 129.1, 129.2, 130.3, 135.0, 144.4, 152.1, 152.3, 152.4, 155.4.

Step 4
Methyl 4-(9-benzyl-9H-purin-6-yl)-4-ethoxy-2-oxo-but-3-enoate (9)

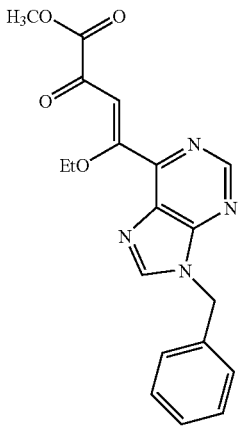

To a stirred solution of 9-benzyl-6-(α-ethoxyvinyl)purine (8) (0.20 g, 0.70 mmol) and pyridine (0.688 mL, 0.72 g, 28.5 mmol) in dry chloroform (10 mL) at 0° C. was added methyl chlorooxoacetate (1.048 g, 0.784 mL, 28.5 mmol) in dry chloroform (5 mL). The reaction mixture was allowed to attain ambient temperature, stirred for 3 days and then washed with water (2×10 mL) and dried over anhydrous sodium sulfate. The solvent was distilled off and the dark reddish syrup was purified by column chromatography. Yield 110 mg, (42%). 11 NMR ($CDCl_3$): 1.53 (t, 3H, $CH_3$, J=6.5 Hz), 3.80 (s, 31-1, $CH_3$), 4.36 (q, 2H, $CH_2$, J=6.5 Hz), 5.49 (s, 2H, benzylic $CH_2$), 6.72 (s, 1H, olefinic CH), 7.36 (m, 5H, Ar—H), 8.07 (s, 1H, purine $C_8$—H), 9.10 (s, 1H, purine $C_2$—H). $^{13}$C NMR ($CDCl_3$): δ 14.1, 31.0, 47.5, 52.9, 67.0, 99.6, 128.0, 128.0, 128.8, 129.3, 129.3, 131.3, 134.7, 145.5, 152.0, 152.6, 162.4, 167.4, and 179.7.

Step 5
Methyl 4-(9-benzyl-9H-purin-6-yl)-2-hydroxy-4-oxo-but-2-enoate (10)

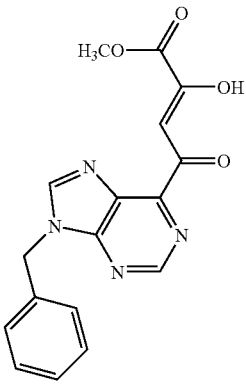

Methyl 4-(9-benzyl-9H-purin-6-yl)-4-ethoxy-2-oxo-but-3-enoate (9) (100 mg, 0.20 mmole) obtained in above step was stirred at room in $CH_2Cl_2$ (20 mL) and treated with $FeCl_3.6H_2O$ (0.125 g, 0.40 mmole). The reaction mixture was stirred at 40° C. for 5 h. Chloroform was distilled off and the resulting residue was treated with 1 N HCl (50 mL) for 1 h and then extracted with EtOAc (4×20 mL). The extract was dried over anhydrous sodium sulfate and the EtOAc distilled off to give a brownish residue which was purified by ion exchange chromatography (diethylamino sephadex anion exchange resin, $CH_3CN:H_2O$, (1:1) eluent). Yield 5.2 mg. Mp 166-167° C. $^1$H NMR ($CDCl_3$) δ 3.99 (s, 3H, $CH_3$), 5.54 (s, 2H, benzylic $CH_2$), 7.35-7.41 (m, 5H, aromatic), 7.9 (s, 1H, olefinic CH), 8.3 (s, 1H, purine $C_8$—H), 9.19 (s, 1H, purine $C_2$—H). $^{13}$C NMR ($CDCl_3$) δ 47.7, 53.4, 101.4, 128.0, 128.0, 128.9, 129.3, 131.8, 134.5, 147.4, 152.3, 154.3, 162.1, 172.8, and 185.7. FAB-HRMS: [M+H]$^+$ Calcd. for $C_{17}H_{15}N_4O_4$ 339.1093. Found 339.1083.

Step 6

Synthesis of 4-(9-benzyl-9H-purin-6-yl)-2-hydroxy-4-oxo-but-3-enoic acid (11)

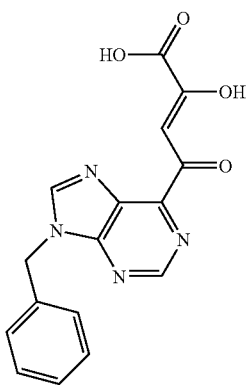

To a stirred solution of methyl 4-(9-benzyl-9H-purin-6-yl)-2-hydroxy-4-oxo-but-3-enoate (10) (17 mg, 0.05 mmol) in THF (5 mL) at 0° C. was added a solution of 1N NaOH (0.5 mL) and the reaction mixture was allowed to stir at 0° C. for 2 h. The reaction mixture was extracted with diethyl ether (2×10 mL) and the aqueous layer was acidified with dilute HCl and extracted with ethyl acetate (2×25 mL). The organic extract washed with brine solution, dried over anhydrous sodium sulfate and concentrated. The crude solid was purified by trituration with diethyl ether to give 4 mg of product. Yield 25%. Mp 152-153° C. $^1$H NMR (CDCl$_3$): δ 5.27 (s, 2H, benzylic CH$_2$), 6.39 (s, 1H, olefenic CH), 7.23-7.29 (m, 5H, Ar—H), 8.78 (s, 1H, purine C$_8$—H), 8.84 (s, 1H, purine C$_2$—H). EIMS (m/z): [M+1] calc for C$_{16}$H$_{13}$N$_4$O$_4$ 325. Found 325.

REPRESENTATIVE EXAMPLE 14

4-(9-Benzyl-9H-purin-8-yl)-2-hydroxy-4-oxobut-2-enoic acid (17)

The relevant scheme is Scheme 4 shown below.

Scheme 4

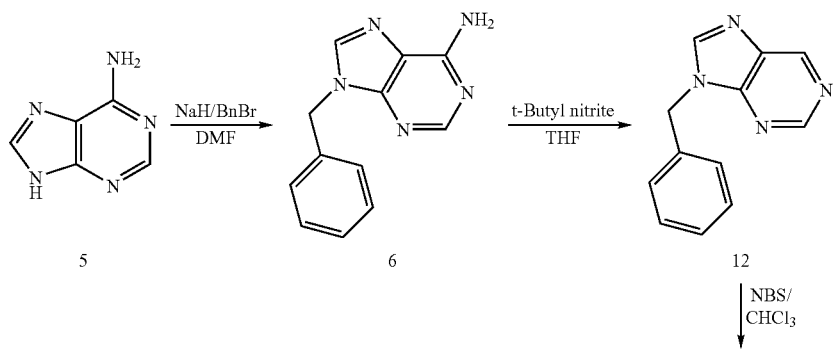

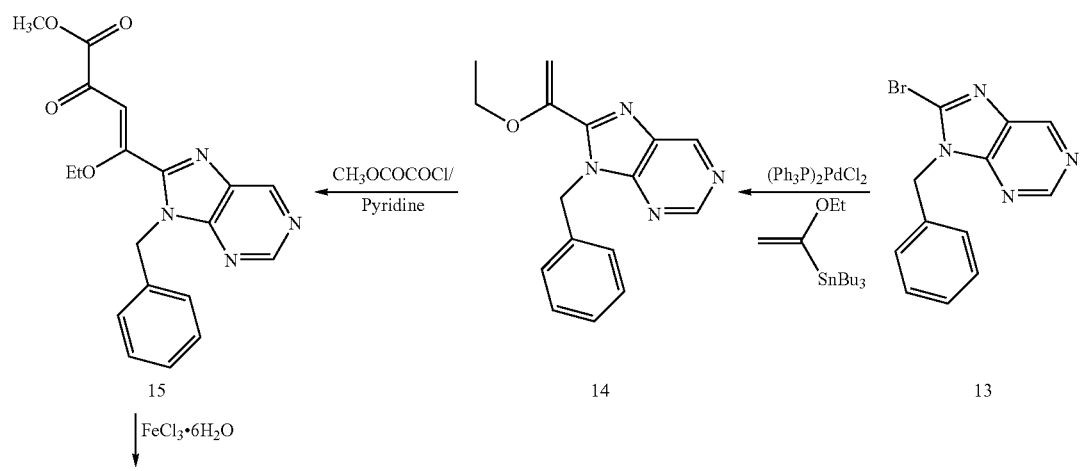

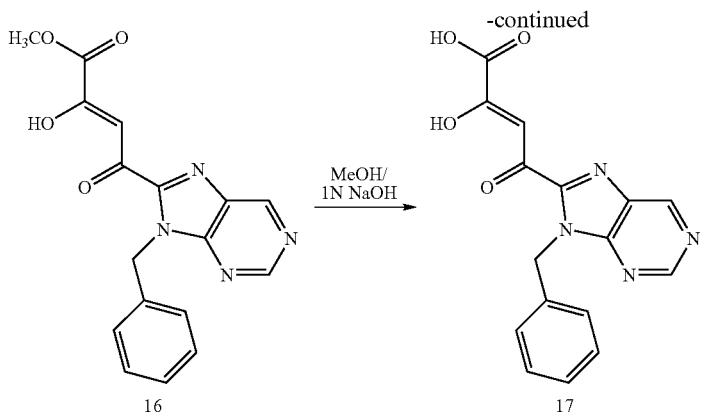

4-(9-Benzyl-9H-purin-8-yl)-2-hydroxy-4-oxobut-2-enoic acid. (17)

Step 1

Described in Step 1 of Example 13

Step 2

Synthesis of 9-benzylpurine (12)

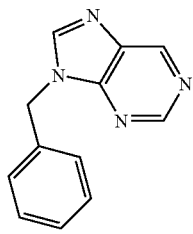

To a stirred suspension of 9-benzyladenine (6) (22.0 g, 97.6 mmol) in anhydrous THF (500 mL) was added t-butyl nitrite (9.34 g, 478.5 mmol) and the reaction mixture heated under an atmosphere of nitrogen at 60-65° C. for 4 h. THF and the excess reagent were distilled off and the residue obtained redissolved in chloroform (100 mL) and washed with brine solution (2×50 mL). The chloroform layer was dried over anhydrous sodium sulfate and distilled off to give a reddish oil, which was purified by flash chromatography on silica gel using EtOAc/hexane (8:2) for elution. Yield 10.68 g (42.3%). Mp 99-100° C. $^1$H NMR (CDCl$_3$): δ 5.49 (s, 2H, CH$_2$), 7.34-7.40 (m, 5H, Ar—H), 8.10 (s, 1H, purine C$_6$—H), 9.06 (s, 1H, purine C$_8$H), 9.20 (s, 1H, purine C$_2$H).

Step 3

9-Benzyl-8-bromo-9H-purine (13)

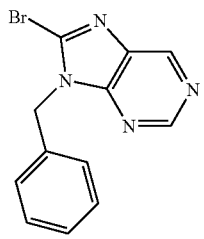

To a stirred solution of 12 (10.68 g, 50.7 mmol) in chloroform (500 mL) was added N-bromosuccinamide (45.20 g, 253.9 mmol) and the reaction mixture stirred under an atmosphere of nitrogen and at reflux temperature for 5 h. The reaction mixture was transferred to a separatory funnel and washed with saturated sodium sulfite solution (2×250 mL) followed by brine solution (2×250 mL). The chloroform fraction was dried over anhydrous sodium sulfate and concentrated and the reddish oil was purified by flash chromatography on silica gel using EtOAc/hexane (4:6) for elution. Yield 6.05 g. (41.2%). Mp 119-121° C.; $^1$H NMR (CDCl$_3$): δ 5.53 (s, 2H, CH$_2$), 7.35-7.39 (m, 5H, Ar—H), 9.03 (s, 1H, purine C$_8$—H), 9.09 (s, 1H, purine C$_2$—H).

Step 4

9-Benzyl-8-(α-ethoxyvinyl)purine (14)

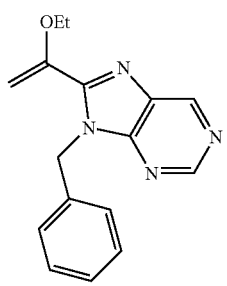

A mixture of 9-benzyl-8-bromopurine 13 (1.0 g, 3.4 mmol) bis(triphenylphosphine)-palladium(II)chloride (0.242 g, 0.30 mmol) and ethoxyvinyl(tributyl)tin (1.49 g, 4.14 mmol) in dry DMF (50 mL) was heated under N$_2$ at 65° C. for 48 h. DMF was distilled off under reduced pressure and the resulting residue was redissolved in EtOAc (50 mL) and filtered through a pad of celite. The EtOAc was distilled off and the residue obtained was purified by flash chromatography. Yield 0.579 g, (59.7%). $^1$H NMR (CDCl$_3$): δ 1.33 (t, 3H, CH$_3$, J=7.5 Hz), 3.99 (q, 2H, CH$_2$, J=13.7 Hz), 4.66 (d, 1H, CH, J=3 Hz), 5.34 (d, 1H, CH, J=3 Hz), 5.48 (s, 2H, benzylic CH$_2$), 7.30-7.38 (m, 5H, Ar—H), 9.09 (s, 1H, purine C$_8$—H), 9.2 (s, 1H, purine C$_2$—H). $^{13}$C NMR (CDCl$_3$): δ 14.2, 47.3, 64.2, 91.8, 126.8, 126.8, 127.7, 128.6, 128.6, 133.1, 136.4, 148.2, 151.2, 151.9, 152.8, 153.0.

Step 5

Synthesis of methyl 4-(9-benzyl-9H-purin-8-yl)-4-ethoxy-2-oxo-but-3-enoate (15)

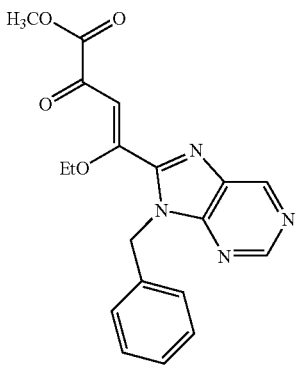

To a stirred solution of 9-benzyl-8-(α-ethoxyvinyl)purine (14) (0.579 g, 2.0 mmol) and pyridine (2.08 g, 24.7 mmol) in dry chloroform (15 mL) at 0° C. was added methyl chlorooxoacetate (3.03 g, 24.7 mmol) in dry chloroform (10 mL). The reaction mixture was allowed to stand in the refrigerator for 15 h. and then washed with (2×20 mL) water and the organic layer dried over anhydrous sodium sulfate. Removal of chloroform gave a dark reddish syrup which was purified by column chromatography. Yield 0.538 g (77%). $^1$H NMR (CDCl$_3$): 1.17 (t, 3H, CH$_3$, J=6.5 Hz), 3.68 (s, 3H, CH$_3$), 3.93 (q, 2H, CH$_2$, J=6.5 Hz), 5.35 (s, 2H, benzylic CH$_2$), 6.45 (s, 1H, olefinic CH), 7.12-7.22 (m, 5H, Ar—H), 8.99 (s, 1H, purine C$_6$—H), 9.08 (s, 1H, purine C$_2$—H). $^{13}$C NMR (CDCl$_3$): δ 13.7, 46.8, 53.2, 67.2, 102.2, 127.8, 128.3, 128.7, 130.9, 133.0, 135.2, 149.1, 149.4, 152.1, 153.5, 162.1, 180.3.

Step 6

Methyl 4-(9-benzyl-9H-purine-8-yl)-2-hydroxy-4-oxo-but-3-enoate (16)

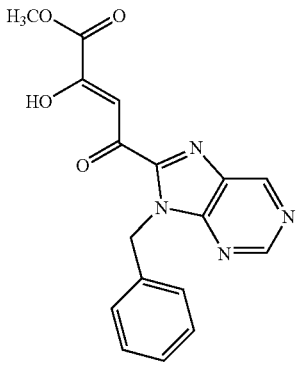

Methyl-4-(9-benzyl-9H-purin-6-yl)-4-ethoxy-2-oxo-but-3-enoate (15) (210 mg, 0.50 mmole) obtained in above step was stirred at room temperature in CH$_2$Cl$_2$ (60 mL) and treated with FeCl$_3$.6H$_2$O (0.262 g, 0.9 mmole). The reaction mixture stirred at 40° C. for 6 h and concentrated and the residue obtained was treated with 1 N HCl (50 mL) for 5 min and extracted with EtOAc (4×20 mL). The organic layer was dried over anhydrous sodium sulfate and concentrated to give a yellowish residue which was purified by ion exchange chromatography. Yield 90 mg. (46%). Mp 137-138° C.; $^1$H NMR (CDCl$_3$) δ 3.98 (s, 3H, CH$_3$), 6.03 (s, 2H, benzylic C$_1$H$_2$), 7.29-7.41 (m, 5H, aromatic), 7.68 (s, 1H, olefinic CH), 9.21 (s, 1H, purine C$_6$—H), 9.39 (s, 1H, purine C$_2$—H). $^{13}$C NMR (CDCl$_3$) δ 47.6, 53.5, 102.2, 128.0, 128.0, 128.1, 128.3, 128.8, 132.8, 135.9, 146.8, 151.6, 152.5, 155.3, 161.9, and 186.2. FAB-HRMS: [M+H]$^+$ Calcd for C$_{17}$H$_{15}$N$_4$O$_4$ 339.1093. Found 339.1099.

Step 7

Synthesis of 4-(9-benzyl-9H-purine-8-yl)-2-hydroxy-4-oxo-but-3-enoic acid (17)

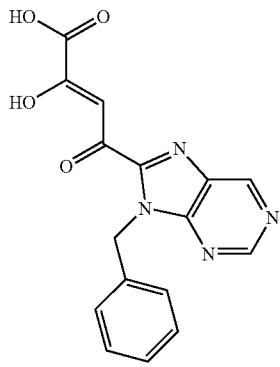

To a stirred solution of methyl 4-(9-benzyl-9H-purin-8-yl)-4-ethoxy-2-oxo-but-3-enoate (16) (0.020 g, 0.059 mmol) in MeOH (3 mL) at 0° C. was added a solution of 1N NaOH (1 mL) and reaction mixture allowed to stir at 0° C. for 30 min and then at ambient temperature for 30 min. The reaction mixture was neutralized with 1 N HCl and the precipitated solid was filtered dried and triturated with chloroform to give yellow solid. Yield: 14 mg (73%). Mp 162-163° C. $^1$H NMR (DMSO-d$_6$): 5.90 (s, 2H, benzylic CH$_2$), 7.26-7.37 (m, 6H, Ar—H and olefinic H), 9.16 (s, 1H, purine C$_6$—H), 9.49 (s, 1H, purine C$_2$—H). NMR (CDCl$_3$): δ 47.6, 101.5, 124.7, 126.6, 127.5, 127.5, 127.5, 128.8, 128.9, 128.9, 137.1, 137.5, 153.0, 155.2, 163.9, 192.9. FAB-HRMS: [M+H]$^+$ Calcd for C$_{16}$H$_{13}$N$_4$O$_4$ 325.0936. Found 325.0924.

REPRESENTATIVE EXAMPLE 15
4-(1,9-Benzyl-6,9-dihydro-6-oxo-1H-purin-8-yl)-4-hydroxy-2-oxo-but-3-enoic acid (24)
The relevant scheme is Scheme 5 shown below.
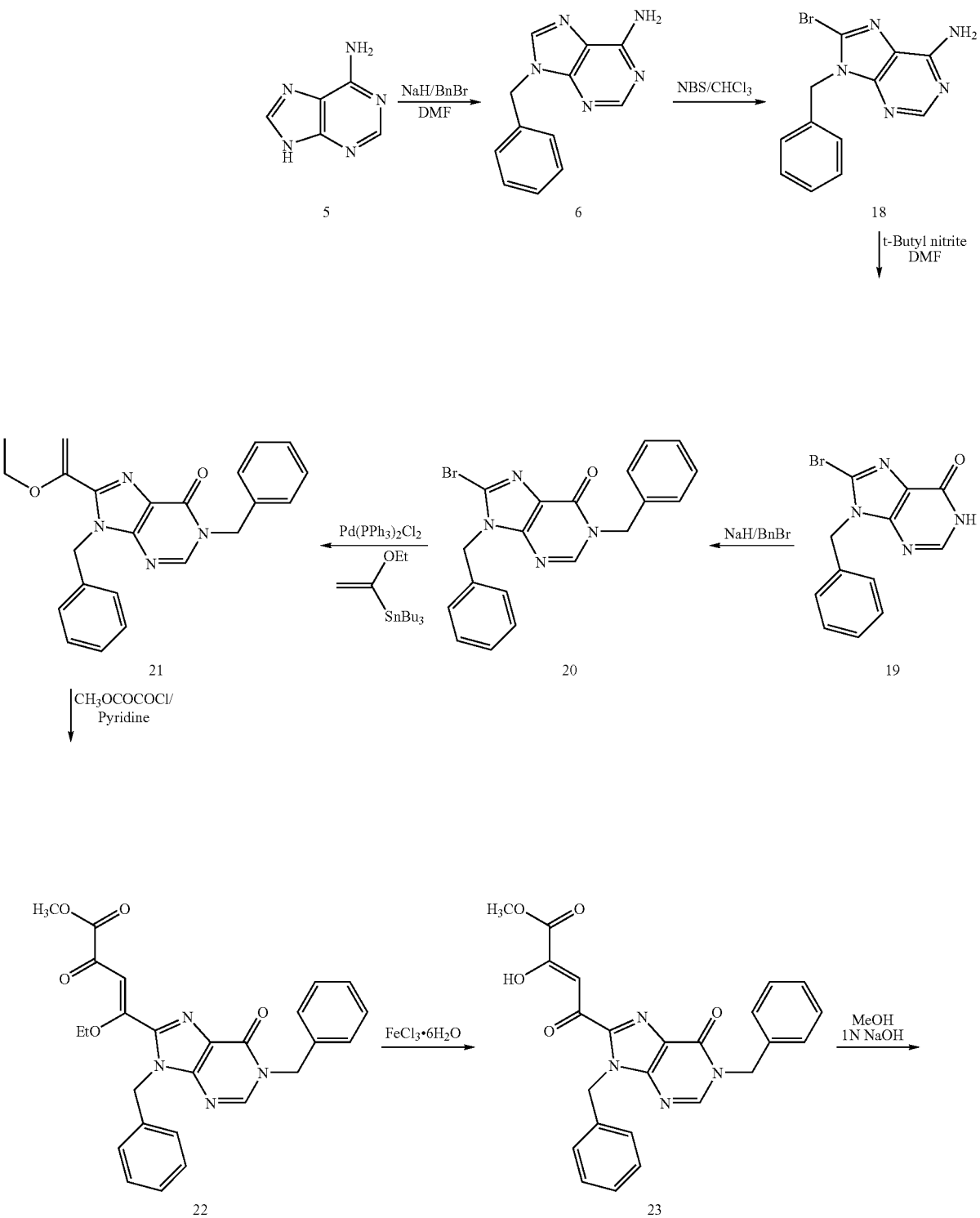

-continued

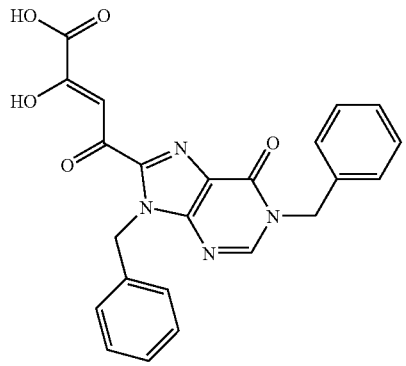

24

Step 1

Described in Step 1 of Example 13

Step 2

Synthesis of 9-benzyl-8-bromoadenine (18)

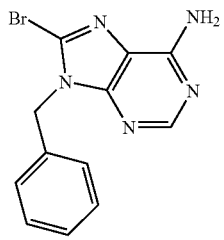

To a stirred solution of 9-benzylpurine (6) (15.0 g, 66.5 mmol) in chloroform (750 mL) was added N-bromosuccinimide (59.26 p. 332.9 mmol) and the reaction mixture vas stirred under an atmosphere of nitrogen at reflux temperature for 3 h. The reaction mixture was then transferred to a separatory funnel and washed with saturated aqueous sodium sulfite (2×250 mL) followed by brine solution (2×250 mL). The chloroform fraction was dried over anhydrous sodium sulfate and concentrated to give a reddish oil, which was purified by flash chromatography on silica gel using EtOAc/hexane (4:6) for elution. Yield 9.72 g. (48%). Mp 199-201° C. $^1$H NMR (CDCl$_3$) δ 5.39 (s, 2H, benzylic CH$_2$), 7.29-7.33 (m, 5H, Ar—H), 8.29 (s, 1H, purine C$_2$—H).

Step 3

9-Benzyl-6,9-dihydro-6-oxo-8-bromopurine (19)

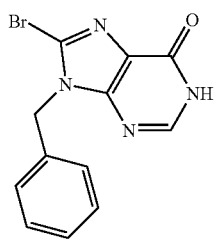

To a stirred suspension of 9-benzyl-8-bromoadenine (18) (2.60 g, 8.5 mmol) in DMF (100 mL) was added t-butyl nitrite (4.31 g, 41.8 mmol) and the reaction mixture heated under an atmosphere of nitrogen at 60-65° C. for 3 h. DMF and the excess reagent were distilled off under reduced pressure and the residue obtained triturated with EtOAc (20 mL). The yellow solid that separated was filtered off and dried under vacuum. Yield 1.41 g (54%) Mp 182-184° C. 1H NMR (CDCl$_3$) δ 5.39 (s, 2H, benzylic CH2), 7.21-7.42 (m, 5H, Ar—H), 8.19 (s, 1H, purine C2—H), 12.59 (s, 1H, NH).

Step 4

1,9-Dibenzyl-6,9-dihydro-6-oxo-8-bromopurine (20)

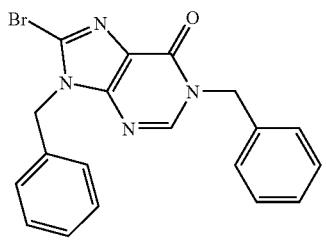

To a suspension of 9-benzyl-6,9-dihydro-6-oxo-8-bromopurine (19) (1.20 g, 3.8 mmol) in dry DMF (25 mL) was added NaH (0.113 g 4.6 mmol) followed by benzyl bromide (0.807 g, 4.6 mmol). The mixture was stirred for 15 h. at room temperature. DMF was removed under reduced pressure and the residue obtained was dissolved in EtOAc (50 mL) and washed with brine solution (2×50 mL). The organic layer was dried over anhydrous sodium sulfate and concentrated to give a yellow syrup, which was purified by column chromatography on silica gel (EtOAc:hexane, 4:6). Yield, 1.20 g (80%). Mp 161-162° C. $^1$H NMR (CDCl$_3$) δ 5.27 (s, 2H, benzylic CH$_2$), 5.34 (s, 2H, benzylic CH), 7.28-7.37 (m, 10H, Ar—H), 8.02 (s, 1H, purine C$_2$—H). $^{13}$C NMR (CDCl$_3$) δ 47.8, 49.3, 124.8, 126.0, 127.7, 127.7, 128.3, 128.3, 128.4, 128.9, 128.9, 129.1, 134.7, 135.8, 147.4, 149.0, 155.5, 184.1. FAB-HRMS: [M+2H] Calcd. for C$_{19}$H$_{17}$BrN$_4$O 397.0487. Found 397.0497.

Step 5

Synthesis of 1,9-dibenzyl-6,9-dihydro-6-oxo-8-(α-ethoxyvinyl)purine (21)

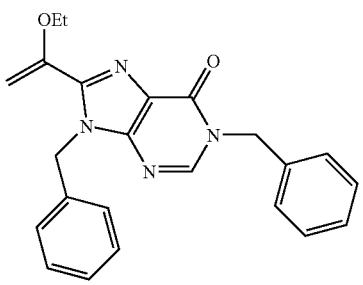

A mixture of 1,9-dibenzyl-6,9-dihydro-6-oxo-8-bromopurine (20) (1.20 g, 3.04 mmol) bis(triphenylphosphine)palladium(II)chloride (0.213 g, 0.3 mmol) and ethoxyvinyl-(tributyl)tin (2.19 g, 6.07 mmol) in dry DMF (50 mL) was heated under $N_2$ at 70° C. for 22 h. DMF was distilled off and the resulting residue dissolved in EtOAc (100 ml) and filtered through a pad of celite. The solvent was distilled off and the residue was purified by flash chromatography (EtOAc:hexane, 6:4). Yield 0.989 g (88%). Mp 167-168° C. $^1$H NMR (CDCl$_3$) δ 1.26 (t, 3H, CH$_3$, J=7.5 Hz), 3.86 (q, 2H, CH$_2$ J=7 Hz), 4.46 (d, 1H, CH, J=2.5 Hz), 5.26 (s, 2H, benzylic CH$_2$), 5.32 (d, 1H, CH$_2$ J=3 Hz), 5.60 (s, 2H, benzylic C$_2$), 7.10-7.37 (m, 10H, Ar—H) 7.99 (s, 1H, purine, C$_2$—H). $^{13}$C NMR (CDCl$_3$) δ 14.1, 47.8, 49.1, 63.8, 90.2, 123.5, 126.6, 126.6, 127.5, 127.5, 128.2, 128.7, 128.7, 128.9, 129.1, 129.1, 136.2, 136.7, 146.2, 146.9, 148.9, 151.9, and 156.6. FAB-HRMS: [M+H]$^+$ Calcd. for C$_{23}$H$_{23}$N$_4$O$_2$ 387.1821. Found 387.1815.

Step 6

Methyl 4-(1,9-benzyl-6,9-dihydro-6-oxo-1H-purin-8-yl)-4-ethoxy-2-oxo-but-3-enoate (22)

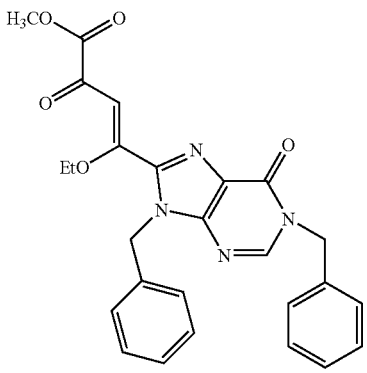

To a stirred solution of 1,9-dibenzyl-6,9-dihydro-6-oxo-8-(ethoxyvinyl)purine (21) (0.620 g, 1.6 mmol) and pyridine (1.61 g, 19.2 mmol) in dry chloroform (30 mL) at 0° C. was added methyl chlorooxoacetate (1.77 mL, 19.2 mmol) in dry chloroform (10 mL) and reaction mixture was allowed to stand in the refrigerator for 48 h. The reaction mixture was washed with (2×100 mL) water and dried over anhydrous sodium sulfate. Chloroform was distilled off to give yellow syrup from which the product was isolated by column chromatograpy (EtOAc:hexane, 4:6). Yield 0.584 g (77%). $^1$H NMR (CDCl$_3$) δ 1.14 (t, 3H, CH$_3$, J=6.5 Hz), 3.66 (s, 3H, CH$_3$), 3.87 (q, 2H, CH$_2$, J=7 Hz), 5.19 (s, 2H, benzylic CH$_2$), 5.23 (s, 2H, benzylic CH$_2$), 6.25 (s, 1H, olefinic CH), 7.09-7.62 (m, 10H, Ar—H), 7.98 (s, 1H, purine, C$_2$—H). $^{13}$C NMR (CDCl$_3$) δ 13.7, 47.3, 49.2, 52.8, 66.6, 102.6, 123.7, 127.4, 127.4, 128.0, 128.0, 128.2, 128.3, 132.1, 132.2, 135.4, 136.0, 143.8, 147.9, 148.6, 156.3, 162.0, 162.7, 181.3. FAB-HRMS: [M+H]$^+$ Calcd. for C$_{26}$H$_{25}$N$_4$O$_5$ 473.1824. Found 473.1810.

Step 7

Methyl 4-(1,9-benzyl-6,9-dihydro-6-oxo-Hl-purin-8-yl)-2-hydroxy-4-oxo-but-3-enoate (23)

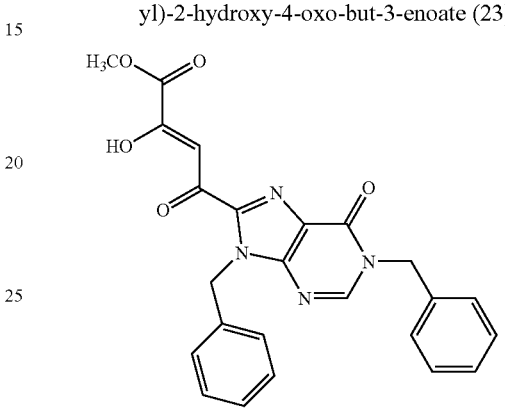

Methyl 4-(1,9-Benzyl-6-9-dihydro-6-oxo-1H-purin-8-yl)-4-ethoxy-2-oxo-but-3-enoate (22) (0.584 g, 1.2 mmole) in CH$_2$Cl$_2$ (150 mL) was treated with FeCl3.6H2O (0.567 g, 2.1 mmole) and the reaction mixture was stirred at 40° C. for 3 h. The solvent was removed and the resulting residue was treated with 1 N HCl (50 mL) for 5 min, extracted with EtOAc (4×20 mL) and dried over anhydrous sodium sulfate. The solvent was removed to give a yellowish residue which was purified by ion exchange chromatography (CH3CN: H2O, 1:1). Yield 0.502 g. (91%). Mp 178-179° C. $^1$H NMR (CDCl$_3$): 3.84 (s, 3H, CH3), 5.21 (s, 2H, benzylic CH2), 5.77 (s, 2H, benzylic CH2), 7.19-7.30 (m, 10H, Ar—H), 7.65 (s, 1H, olefinic CH), 8.07 (s, 1H, purine C2—H). $^{13}$C NMR (CDCl$_3$): δ 48.1, 49.5, 53.2, 102.5, 119.3, 124.8, 127.9, 127.9, 128.2, 128.2, 128.4, 128.7, 128.7, 128.8, 129.2, 129.2, 135.5, 135.9, 143.1, 149.4, 150.0, 156.7, 162.2, 162.2, 184.1, 185.9. FAB-HRMS: [M+H]$^+$ Calcd. for C24H21N4O5 445.1511. Found 445.1520.

Step 8

Synthesis of 4-(1,9-benzyl-6,9-dihydro-6-oxo-1H-purin-8-yl)-4-hydroxy-2-oxo-but-3-enoic acid (24)

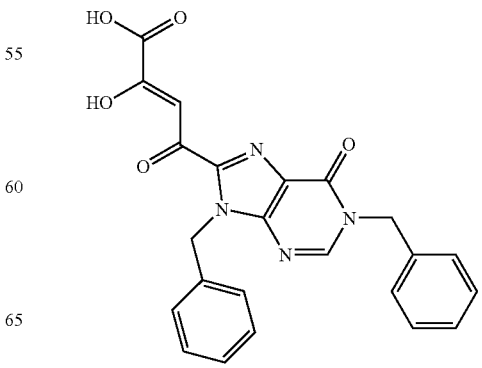

To a stirred solution of 4-(1,9-benzyl-6,9-dihydro-6-oxo-1H-1-purin-8-yl)-2-ethoxy-4-oxo-but-3-enoic acid methyl ester (23) (0.110 g, 0.24 mmol) in MeoH (10 mL) at 0° C. was added a solution of 1N NaOH (2 mL). The reaction mixture was allowed to stir at 0° C. for 30 min and then at room temperature for 1 h. This was followed by neutralization with 1 N HCl and the solid that separated out was filtered dried and triturated with diethyl ether to give yellow solid. Yield 91 mg (86%). Mp 167° C. (decomp.). $^1$H NMR (DMSO-d$_6$) δ 5.27 (s, 2H, benzylic CH$_2$), 5.80 (s, 2H, benzylic CH$_2$), 7.25 (s, 1H, olefinic CH), 7.27-7.37 (m, 10H, Ar—H), 8.77 (s, 1H, purine C$_2$—H). $^{13}$C NMR (CDCl$_3$) δ 47.9, 49.4, 101.4, 123.9, 127.6, 127.6, 128.2, 128.2, 128.7, 128.9, 129.1, 137.2, 137.2, 150.4, 151.6, 156.5, 163.9, 176.0, 179.5. FAB-HRMS: [M+H]$^+$ Calcd for C$_{23}$H$_{19}$N$_4$O$_5$ 431.1355. Found 431.1373.

What is claimed is:

1. A compound according to the general structure of formula I:

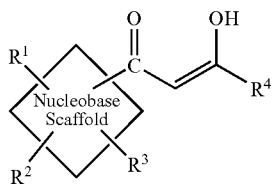

wherein the nucleobase scaffold is purine:

R$^1$ and R$^2$ are each independently H, C$_{1-6}$ alkyl, C$_{1-6}$ fluoroalkyl, unsubstituted or substituted C$_{5-6}$ cycloalkyl, C$_{1-6}$ alkenyl, unsubstituted or substituted phenyl, unsubstituted or substituted benzyl, C$_{2-6}$ alkyl phenyl which phenyl moiety may be optionally substituted, unsubstituted or substituted heteroaryl, C$_{1-6}$ alkyl substituted with a heteroaryl group which heteroaryl group is optionally substituted, C$_{1-6}$ alkyl S(O)R or alkyl (SO$_2$)R where R is alkyl, phenyl or substituted phenyl, C$_{1-6}$alkyl CO$_2$R$^a$ where R$^a$ is C$_{1-6}$ alkyl or H, C$_{1-6}$alkyl COR$^{a'}$ where R$^{a'}$ is C$_{1-6}$ alkyl;

R$^3$ is selected from H, C$_{1-6}$ alkyl, halogen, hydroxyl, unsubstituted or substituted benzyl, or unsubstituted or substituted phenylthio;

R$^4$ is CO$_2$R$^c$ or P(O)(OR$^c$)(OR$^c$), where each R$^c$ is independently from H and C$_{1-6}$ alkyl, or a pharmaceutically acceptable salts thereof.

2. The compound of claim 1 according to the structure:

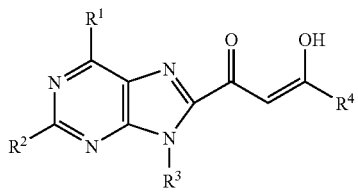

wherein R$^1$, R$^2$ and R$^3$ are each independently H, a benzyl group or substituted benzyl group with 1 to 3 substituents on the aromatic ring selected from halogen, hydroxyl, methoxy, methyl, ethyl, propyl, CF$_3$ or wherein R$^1$, R$^2$ and R$^3$ are each independently —CH$_2$R$^b$ where R$^b$ is a 5- or 6-membered heteroaromatic ring;

wherein R$^4$ is CO$_2$R where R is selected from H and C$_{1-6}$ alkyl, or a pharmaceutically acceptable salts thereof.

3. The compound of claim 1 according to the structure:

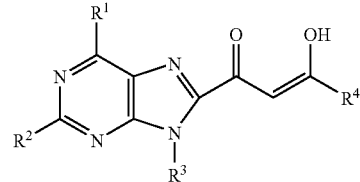

wherein R$^1$, R$^2$ and R$^3$ are each independently H, a benzyl group or substituted benzyl group with 1 to 3 substituents on the aromatic ring selected from halogen, hydroxyl, methoxy, methyl, ethyl, propyl, CF$_3$ or wherein R$^1$, R$^2$ and R$^3$ are each independently —CH$_2$R$^b$ where R$^b$ is a 5- or 6-membered heteroaromatic ring or a phenyl group;

wherein R$^4$ is P(O)(OR)(OR) or CO$_2$R, where the R groups could be the same or not and are selected from H and C$_{1-6}$ alkyl, or a pharmaceutically acceptable salts thereof.

4. The compound of claim 1 according to the structure:

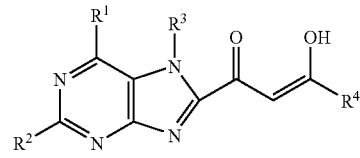

wherein R$^1$, R$^2$ and R$^3$ are each independently H, a benzyl group or substituted benzyl group with 1 to 3 substituents on the aromatic ring selected from halogen, hydroxyl, methoxy, methyl, ethyl, propyl, CF$_3$ or wherein R$^1$, R$^2$ and R$^3$ are each independently —CH$_2$ R$^b$ where R$^b$ is a 5- or 6-membered heteroaromatic ring or a phenyl group;

wherein R$^4$ is CO$_2$R where R is selected from H and C$_{1-6}$ alkyl, or a pharmaceutically acceptable salts thereof.

5. The compound of claim 1 according to the structure:

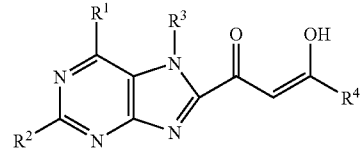

wherein R$^1$, R$^2$ and R$^3$ are each independently H, a benzyl group or substituted benzyl group with 1 to 3 substituents on the aromatic ring selected from halogen, hydroxyl, methoxy, methyl, ethyl, propyl, CF$_3$ or wherein R$^1$, R$^2$ and R$^3$ are each independently —CH$_2$ R$^b$ where R$^b$ is a 5- or 6-membered heteroaromatic ring or a phenyl group;

wherein R$^4$ is P(O)(OR)(OR), where the R groups could be the same or not and are selected from H and C$_{1-6}$ alkyl, or a pharmaceutically acceptable salts thereof.

6. A pharmaceutical composition for treating an HIV infection, comprising a therapeutically effective amount of a compound according to claim 1 and a pharmaceutically acceptable carrier, additive or excipient.

7. The pharmaceutical composition of claim 6 wherein said composition treats said HIV infection by inhibiting HIV integrase in the human host.

8. A pharmaceutical composition comprising a therapeutically effective amount of a compound according to claim 1 in combination with a therapeutically effective amount of at least one compound selected from the group consisting of i) an additional anti-HIV agent, ii) an anti-infective agent other than an anti-HIV agent and iii) an immunomodulator, and a pharmaceutically acceptable carrier, additive or excipient.

9. The composition of claim 8 wherein said anti-infective agent is an antiviral agent selected from the group consisting of a protease inhibitor, a reverse transcriptase inhibitor or a combination thereof.

10. The composition of claim 9 wherein said reverse transcriptase inhibitor is a nucleoside compound.

11. The composition of claim 9 wherein said reverse transcriptase inhibitor is a non-nucleoside compound.

12. The composition of claim 6 in oral or parenteral dosage form.

13. The composition of claim 8 in oral or parenteral dosage form.

14. The composition according to claim 6 formulated for administration as an inhalation spray or a rectal suppository.

15. The composition according to claim 8 formulated for administration as an inhalation spray or a rectal suppository.

16. A method of treating an HIV infection in a patient, said method comprising administering to said patient an effective amount of a composition according to claim 6 to said patient.

17. A method of treating an HIV infection in a patient, said method comprising administering to said patient an effective amount of a composition according to claim 7 to said patient.

18. A method of treating an HIV infection in a patient, said method comprising administering to said patient an effective amount of a composition according to claim 8 to said patient.

19. A method of reducing the likelihood of an HIV infection in a patient at risk for said infection, said method comprising administering to said patient an effective amount of a composition according to claim 6 to said patient.

20. A method of reducing the likelihood of an HIV infection in a patient at risk for said infection, said method comprising administering to said patient an effective amount of a composition according to claim 8 to said patient.

21. A method of treating a patient with AIDS or ARC comprising administering to said patient a therapeutically effective amount of the composition according to claim 6.

22. A method of treating a patient with AIDS or ARC comprising administering to said patient a therapeutically effective amount of the composition according to claim 7.

23. A method of inhibiting HIV integrase in a subject in need thereof, said method comprising administering to said subject a therapeutically effective amount of a compound according to claim 1.

24. The method according to claim 23 wherein said subject is a human.

25. A pharmaceutical composition for treating an HIV infection, comprising a therapeutically effective amount of a compound according to claim 2 and a pharmaceutically acceptable carrier, additive or excipient.

26. A pharmaceutical composition for treating an HIV infection, comprising a therapeutically effective amount of a compound according to claim 3 and a pharmaceutically acceptable carrier, additive or excipient.

27. A pharmaceutical composition for treating an HIV infection, comprising a therapeutically effective amount of a compound according to claim 4 and a pharmaceutically acceptable carrier, additive or excipient.

28. A pharmaceutical composition for treating an HIV infection, comprising a therapeutically effective amount of a compound according to claim 5 and a pharmaceutically acceptable carrier, additive or excipient.

29. The composition of claim 8 wherein said additional anti-HIV agent is a compound selected from the group consisting of a protease inhibitor, a reverse transcriptase inhibitor or a combination thereof.

30. The composition of claim 29 wherein said reverse transcriptase inhibitor is a nucleoside compound.

31. The composition of claim 29 wherein said reverse transcriptase inhibitor is a non-nucleoside compound.

* * * * *